(12) United States Patent
Ryu et al.

(10) Patent No.: US 11,903,307 B2
(45) Date of Patent: Feb. 13, 2024

(54) ORGANIC COMPOUND, AND LIGHT-EMITTING DIODE AND LIGHT-EMITTING DEVICE INCLUDING THE SAME

(71) Applicant: LG Display Co., Ltd., Seoul (KR)

(72) Inventors: Young-Ju Ryu, Paju-si (KR); Kyu-Nam Kim, Paju-si (KR); Jae-Hyun Park, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 633 days.

(21) Appl. No.: 16/193,715

(22) Filed: Nov. 16, 2018

(65) Prior Publication Data
US 2019/0157566 A1    May 23, 2019

(30) Foreign Application Priority Data

Nov. 17, 2017  (KR) .................. 10-2017-0154102

(51) Int. Cl.
*H10K 85/60* (2023.01)
*C07D 495/04* (2006.01)
(Continued)

(52) U.S. Cl.
CPC ......... *H10K 85/636* (2023.02); *C07D 495/04* (2013.01); *H10K 85/633* (2023.02);
(Continued)

(58) Field of Classification Search
CPC ............. C07D 495/04; H01L 51/0068; H01L 51/0074; H10K 85/6576; H10K 85/655
See application file for complete search history.

(56) References Cited

U.S. PATENT DOCUMENTS 8,343,636 B2    1/2013  Jen et al.
9,112,157 B2    8/2015  Brown et al.
(Continued)

FOREIGN PATENT DOCUMENTS

WO    2013/173396 A2    11/2013

OTHER PUBLICATIONS

Cheng, Y. et al, Thermally Cross-Linkable Hole-Transporting Materials on Conducting Polymer: Synthesis, characterizationa nd applications for polymer light-emitting devices, Chem. Mater. Dec. 29, 2007, 20, 2, 413-422. (Year: 2007).*

*Primary Examiner* — Sean M DeGuire
(74) *Attorney, Agent, or Firm* — Seed IP Law Group LLP

(57) ABSTRACT

Compounds, and polymers thereof, useful dopants for light emitting diodes and light emitting display devices are disclosed. The compounds have the following structure Formula 1:

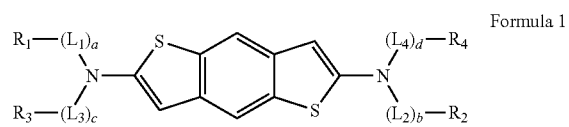

Formula 1 wherein $R_1$, $R_2$, $R_3$, $R_4$, $L_1$, $L_2$, $L_3$, $L_4$, a, b, c and d are as defined herein. Light emitting diodes including compounds of Formula 1 (and polymers thereof, i.e., compounds of Formula 3), light emitting devices including the same as well as methods associated with preparation and use of such compounds, polymers and devices are also provided.

10 Claims, 8 Drawing Sheets

(51) Int. Cl.
*H10K 50/115* (2023.01)
*H10K 50/15* (2023.01)

(52) U.S. Cl.
CPC .......... *H10K 50/115* (2023.02); *H10K 50/156* (2023.02); *H10K 85/626* (2023.02); *H10K 85/6572* (2023.02); *H10K 85/6576* (2023.02)

(56) References Cited

U.S. PATENT DOCUMENTS

| | | | | |
|---|---|---|---|---|
| 2008/0134450 A1* | 6/2008 | Glenn | .................. | A61K 8/49 |
| | | | | 8/423 |
| 2011/0049477 A1* | 3/2011 | Meng | .................. | C08G 61/126 |
| | | | | 257/40 |
| 2013/0105769 A1* | 5/2013 | Lim | .................. | H10K 85/6572 |
| | | | | 546/171 |
| 2013/0324716 A1* | 12/2013 | Brown | .................. | C07D 495/14 |
| | | | | 564/426 |
| 2017/0069850 A1* | 3/2017 | Hwang | .................. | H01L 51/0073 |

\* cited by examiner

ORGANIC COMPOUND, AND LIGHT-EMITTING DIODE AND LIGHT-EMITTING DEVICE INCLUDING THE SAME

CROSS-REFERENCE TO RELATED APPLICATIONS

This application claims the benefit under 35 U.S.C. § 119(a) of Korean Patent Application No., 10-2017-0154102, filed in Korea on Nov. 17, 2017, which is incorporated herein by reference in its entirety.

BACKGROUND

Technical Field

The present disclosure relates to an organic compound, and more particularly, to an organic compound with enhanced charge transfer properties, and a light-emitting diode and a light-emitting device each using the same and thus exhibiting enhanced luminous efficiency.

Description of the Related Art

Among a variety of flat panel display devices developed to replace existing cathode ray tubes (CRTs), organic light-emitting diode (OLED) display devices and quantum dot light-emitting diode (QLED) display devices can have a thin structure and have low power consumption, and thus are attracting attention as next-generation display devices that replace liquid crystal display (LCD) devices. These OLEDs or QLEDs can be installed on a flexible transparent substrate such as a plastic substrate, can be operated at low voltage (10 V or less), have relatively low power consumption, and exhibit excellent color purity.

FIG. 1 is a schematic diagram illustrating bandgap energy levels of materials constituting electrodes and an emissive layer of a general LED. Referring to FIG. 1, the LED includes an anode and a cathode that face each other, an emitting material layer (EML) located between the anode and the cathode, a hole injection layer (HIL) and a hole transport layer (HTL) that are located between the anode and the EML, and an electron transport layer (ETL) located between the cathode and the EML.

OLEDs or QLEDs are devices in which when charge carriers are injected into an emissive layer disposed between an electron injection electrode (a cathode) and a hole injection electrode (an anode), electron-hole pairs are formed, and then disappear, whereby light is emitted. An EML constituting an emissive layer is formed of a luminescent material, and holes and electrons respectively injected from an anode and a cathode recombine in the EML to form excitons. The luminescent material included in the EML is in an excited state by this energy, energy transition from the excited state to a ground state occurs in the luminescent material, and the generated energy is emitted as light.

Meanwhile, the HIL and the HTL inject and transport holes, which are positively charged carriers, from the anode to the EML, and the ETL injects and transports electrons, which are negatively charged carriers, from the cathode to the EML. In order for holes and electrons to be injected and transported into the EML, each layer should be formed of a material having appropriate bandgap energy. Conventionally, an emissive layer constituting an OLED or a QLED is formed through a deposition process, but recently, a solution process that may reduce waste of an organic material and does not require a color filter has been used to form an emissive layer.

For example, the HIL may be formed of poly(3,4-ethyl-enedioxythiophene) polystyrene sulfonate (PEDOT:PSS), the HTL may be formed of poly[(9,9-dioctylfluorenyl-2,7-diyl)-co-(4,4'-(N-(4-sec-butylphenyl)diphenylamine (TFB) and the ETL may be formed of 2-biphenyl-4-yl-5-(4-t-butylphenyl)-1,3,4-oxadiazole (PBD).

When thin films are formed through a solution process to manufacture a light-emitting diode having a structure in which a plurality of layers are stacked, a lower layer may be dissolved in a solvent used to form an upper layer, and mixing of materials may occur at an interface between the upper layer and the lower layer. That is, when neighboring emissive layers of a light-emitting diode manufactured through a solution process are stacked, a compatible solvent capable of dispersing and dissolving both a luminescent material of each of the neighboring emissive layers and/or a charge transporting material cannot be used.

However, a hole transporting material constituting an HTL, and a luminescent material constituting an EML, e.g., quantum dots (QDs) have poor dispersibility with respect to a polar solvent, and thus a solution process is performed in a state in which both are dispersed in a non-polar solvent. Thus, when an HTL is formed by a solution process and an EML is formed on the HTL using a luminescent material dispersed in a non-polar solvent, a hole transporting material used to form the HTL in addition to the luminescent material is mixed with the non-polar solvent used to form the EML.

Since the hole transporting material and the luminescent material are mixed, the HTL is not distinctly distinguished from the EML. An interface between the HTL and the EML is unclearly formed and has a rough sectional shape. Accordingly, an interface between an emissive layer and a neighboring layer that constitute a light-emitting diode also has a rough cross-section, rather than a smooth cross-section, and overall morphological characteristics of the light-emitting diode deteriorate. Thus, since holes and electrons cannot be injected in balance according to a region of the light-emitting diode, holes and electrons are recombined in the EML and thus disappear, thus not emitting light. As a result, luminous efficiency of the light-emitting diode is reduced, and a high driving voltage is required to realize desired luminescence, which causes an increase in power consumption.

BRIEF SUMMARY

Accordingly, the present disclosure is directed to an organic compound, and a light-emitting diode and a light-emitting device including the same that obviate one or more of the problems due to the limitations and disadvantages of the related art.

An object of the present disclosure is to provide an organic compound that is completely cured and thus prevent materials constituting a light-emitting diode from being mixed or blended.

Another object of the present disclosure is to provide a light-emitting diode and light-emitting device that prevent materials from being mixed or blended between emissive layers formed by a solution process and constituting the light-emitting diode so that one emissive layer can clearly be distinguished from another, and thus exhibit enhanced roughness characteristics and enhanced morphological characteristics.

Another object of the present disclosure is to provide a light-emitting diode and a light-emitting device that exhibit enhanced luminous efficiency and can be operated at low voltage.

According to an aspect of an embodiment, there is provided an organic compound having hole transfer properties and capable of forming cross-links by a curing process.

For example, in the organic compound of the present disclosure, a functional group linked to a nitrogen atom linked to a dibenzothiophene core may be substituted with a vinyl group having an ethylenic double bond.

According to an aspect of another embodiment, there is provided a light-emitting diode in which a cured product of the above-described organic compound is used in a hole transfer layer of an emissive layer.

In one exemplary embodiment, the cured product of the organic compound may be used in a hole transport layer.

According to an aspect of another embodiment, there is provided a light-emitting device (e.g., a light-emitting display device) including a substrate; the above-described light-emitting diode disposed on an upper portion of the substrate; and a driving device disposed between the substrate and the light-emitting diode and connected to the light-emitting diode.

Advantages and features of the disclosure will be set forth in part in the description, which follows and in part will become apparent to those having ordinary skill in the art upon examination of the following or may be learned from practice of the disclosure. Other advantages and features of the embodiments herein may be realized and attained by the structure particularly pointed out in the written description and claims hereof as well as the appended drawings.

It is to be understood that both the foregoing general description and the following detailed description are explanatory, and are intended to provide further explanation of the embodiments as claimed.

BRIEF DESCRIPTION OF THE SEVERAL VIEWS OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
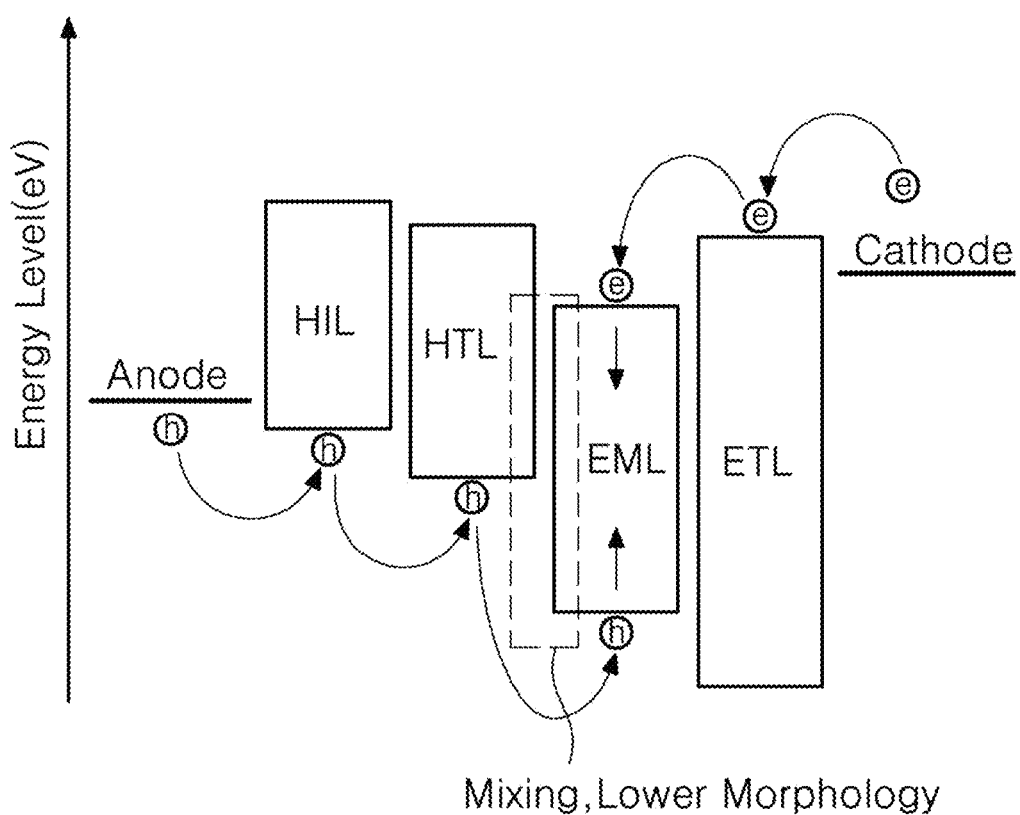
FIG. 1 is a schematic diagram illustrating energy levels of materials constituting electrodes and an emissive layer of an existing light-emitting diode, and schematically illustrates a problem in which materials constituting, in particular, a hole transport layer (HTL) and an emitting material layer (EML) are mixed in a light-emitting diode manufactured by a solution process.

Reference will now be made in detail to embodiments of the present disclosure, examples of which are illustrated in the accompanying drawings. In the following description, when a detailed description of well-known functions or configurations related to this document is determined to unnecessarily obscure the gist of an embodiment of the disclosure, the detailed description thereof will be omitted. The progression of processing steps and/or operations described is an example; however, the sequence of steps and/or operations is not limited to that set forth herein and may be changed as is known in the art, with the exception of steps and/or operations necessarily occurring in a certain order. Like reference numerals designate like elements throughout. Names of the respective elements used in the following explanations are selected only for convenience of writing the specification and thus may be different from those used in actual products.

Hereinafter, the present disclosure will be described with reference to the accompanying drawings as needed.

In a light-emitting diode, a compound used as a charge transporting material needs to have high charge mobility and inject balanced numbers of charge carriers into an emitting material layer. In addition, when a light-emitting diode is manufactured by a solution process, it may be advantageous in terms of luminous efficiency or other characteristics if it is possible to prevent materials used in neighboring layers from being mixed. An organic compound according to an embodiment of the present disclosure may satisfy these properties and be represented by Formula 1 below:

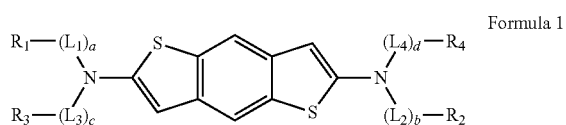

Formula 1

Wherein $R_1$ and $R_2$ are each independently selected from the group consisting of protium, deuterium, tritium, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_5$-$C_{30}$ aryl group, an unsubstituted or substituted $C_4$-$C_{30}$ heteroaryl group, an unsubstituted or substituted $C_5$-$C_{30}$ aralkyl group, an unsubstituted or substituted $C_4$-$C_{30}$ heteroaralkyl group, an unsubstituted or substituted $C_5$-$C_{30}$ aryloxy group, an unsubstituted or substituted $C_4$-$C_{30}$ heteroaryloxy group, an unsubstituted or substituted $C_5$-$C_{30}$ aryl amino group, and an unsubstituted or substituted $C_4$-$C_{30}$ heteroaryl amino group; $R_3$ and $R_4$ are each independently a $C_2$-$C_5$ alkenyl; $L_1$, $L_2$, $L_3$, and $L_4$ are each independently selected from the group consisting of an unsubstituted or substituted $C_1$-$C_{20}$ alkylene group, an unsubstituted or substituted $C_1$-$C_{20}$ alkoxylene group, an unsubstituted or substituted $C_5$-$C_{30}$ arylene group, an unsubstituted or substituted $C_4$-$C_{30}$ heteroarylene group, an unsubstituted or substituted $C_5$-$C_{30}$ aralkylene group, and an unsubstituted or substituted $C_4$-$C_{30}$ heteroaralkylene group; a and b are each independently 0 or 1; and c and d are each independently 1 or 2.

As used herein, the term "unsubstituted" means that hydrogen atoms are bonded, and in this case, the hydrogen atoms include protium, deuterium, and tritium.

With respect to the term "substituted" as used herein, the substituent may be, for example, a $C_1$-$C_{20}$ alkyl group that is unsubstituted or substituted with a halogen atom, a cyano group, and/or a nitro group; a $C_1$-$C_{20}$ alkoxy group, a halogen atom, a cyano group, or an alkyl halide group (e.g., —$CF_3$) that is unsubstituted or substituted with a halogen atom, a cyano group, and/or a nitro group; a hydroxyl group, a carboxyl group, a carbonyl group, an amino group, a $C_1$-$C_{10}$ alkyl-substituted amino group, a $C_5$-$C_{30}$ aryl-substituted amino group, a $C_4$-$C_{30}$ heteroaryl-substituted amino group, a nitro group, a hydrazyl group, a sulfonic acid group, a $C_1$-$C_{20}$ alkylsilyl group, a $C_1$-$C_{20}$ alkoxysilyl group, a $C_3$-$C_{30}$ cycloalkylsilyl group, a $C_5$-$C_{30}$ arylsilyl group, a $C_4$-$C_{30}$ heteroarylsilyl group, a $C_5$-$C_{30}$ aryl group, a $C_4$-$C_{30}$ heteroaryl group, a $C_5$-$C_{30}$ aralkyl group, a $C_4$-$C_{30}$ heteroaralkyl group, a $C_5$-$C_{30}$ aralkoxy group, or a $C_4$-$C_{30}$ heteroaralkoxy group that is unsubstituted or substituted with a halogen atom, a cyano group, and/or a nitro group; or the like, but the present disclosure is not limited to the above examples.

As used herein, the term "hetero" used in the terms "heteroaromatic ring," "hetero cycloalkylene group," "heteroarylene group," "heteroaralkylene group," "hetero aryloxylene group," "hetero cycloalkyl group," "heteroaryl group," "heteroaralkyl group," "heteroaraloxyl group," "heteroaryl amino group," and the like means that at least one, e.g., one to five of carbon atoms constituting such an aromatic or alicyclic ring is substituted with at least one heteroatom selected from the group consisting of N, O, and S.

According to one exemplary embodiment, in Formula 1, each of $R_1$ and $R_2$ may be independently an aromatic substituent. For example, the aromatic substituent that may constitute $R_1$ and $R_2$ may be an aryl group or a heteroaryl group. In particular, each of $R_1$ and $R_2$ may be independently an aromatic ring such as an unfused or fused aryl group such as an unsubstituted or substituted phenyl group, an unsubstituted or substituted biphenyl group, an unsubstituted or substituted terphenyl group, an unsubstituted or substituted tetraphenyl group, an unsubstituted or substituted naphthyl group, an unsubstituted or substituted anthracenyl group, an unsubstituted or substituted indenyl group, an unsubstituted or substituted phenalenyl group, an unsubstituted or substituted phenanthrenyl group, an unsubstituted or substituted azulenyl group, an unsubstituted or substituted pyrenyl group, an unsubstituted or substituted fluorenyl group, an unsubstituted or substituted tetracenyl group, an unsubstituted or substituted indacenyl group, or an unsubstituted or substituted spirofluorenyl group; and/or a heteroaromatic ring such as an unfused or fused heteroaryl group such as a pyrrolyl group, a pyridinyl group, a pyrimidinyl group, a pyrazinyl group, a pyridazinyl group, a triazinyl group, a tetrazinyl group, an imidazolyl group, a pyrazolyl group, an indolyl group, a carbazolyl group, a benzocarbazolyl group, a dibenzocarbazolyl group, an indolocarbazolyl group, an indenocarbazolyl group, a benzofuranocarbazolyl group, a benzothienocarbazolyl group, a quinolinyl group, an isoquinolinyl group, a phthalazinyl group, a quinoxalinyl group, a cinnolinyl group, a quinazolinyl group, a benzoquinolinyl group, a benzoisoquinolinyl group, a benzoquinazolinyl group, a benzonquinoxalinyl group, an acridinyl group, a phenanthrolinyl group, a furanyl group, a pyranyl group, an oxazinyl group, an oxazolyl group, an oxadiazolyl group, a triazolyl group, a dioxynyl group, a benzofuranyl group, a dibenzofuranyl group, a thiopyranyl group, a thiazinyl group, a thiophenyl group, or a N-substituted spirofluorenyl group.

In addition, in Formula 1, $R_1$ and/or $R_2$ may be substituted with an unsubstituted or substituted $C_1$-$C_{20}$ alkyl group, or an aromatic functional group. For example, this functional group may be a $C_1$-$C_{20}$ alkyl group or a aryl group such as a phenyl group, a biphenyl group, a terphenyl group, a naphthyl group, an anthracenyl group, a fluorenyl group, or a spirofluorenyl group that is unsubstituted or substituted with at least one functional group selected from a halogen atom such as fluorine, a nitro group, and a cyano group; and/or a heteroaryl group such as a benzothiopheneyl group, a dibenzothiopheneyl group, a benzofuranyl group, a dibenzofuranyl group, a pyrrolyl group, a pyridinyl group, a pyrimidinyl group, a pyrazinyl group, a pyridazinyl group, a triazinyl group, a tetrazinyl group, an imidazolyl group, a pyrazolyl group, an indolyl group, a carbazolyl group, a benzocarbazolyl group, a dibenzocarbazolyl group, an indolocarbazolyl group, an indenocarbazolyl group, a benzofuranocarbazolyl group, a benzothienocarbazolyl group, a quinolinyl group, an isoquinolynyl group, a phthalazinyl group, a quinoxalinyl group, a cinnolinyl group, a quinazolinyl group, a phthalazinyl group, a quinoxalinyl group, a benzoquinolinyl group, a benzoisoquinolinyl group, a benzoquinazolinyl group, or a benzoquinoxalinyl group that is substituted with at least one functional group selected from a halogen atom such as fluorine, a nitro group, and/or a cyano group.

In some embodiments, $R_1$ is an unsubstituted or substituted $C_5$-$C_{30}$ aryl group or an unsubstituted or substituted $C_4$-$C_{30}$ heteroaryl group. For example, in some embodiments, $R_1$ has one of the following structures:

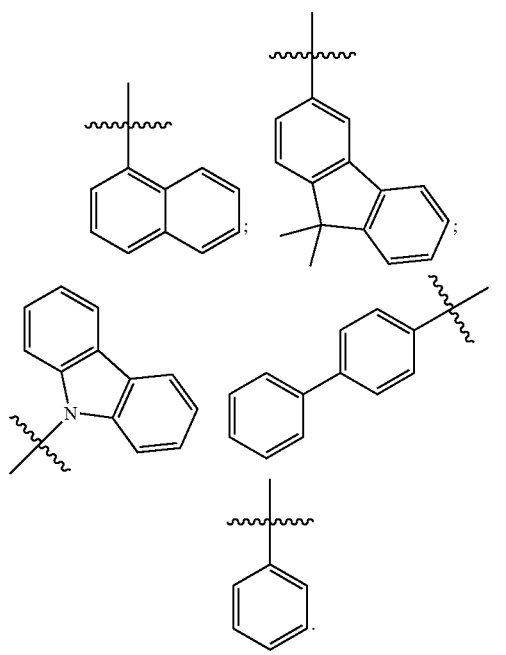

In other embodiments, R₂ is an unsubstituted or substituted $C_5$-$C_{30}$ aryl group or an unsubstituted or substituted $C_4$-$C_{30}$ heteroaryl group. For example, in some embodiments, $R_2$ has one of the following structures:

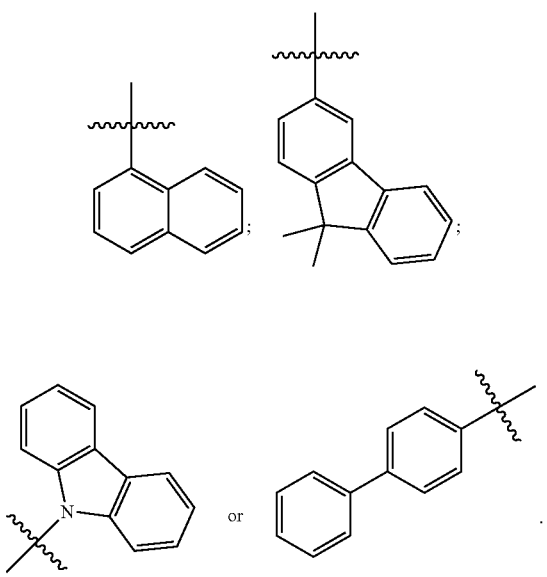

$R_3$ and $R_4$ are each independently $C_2$-$C_5$ alkenyl. In some embodiments, $R_3$ has the following structure:

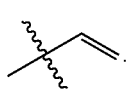 [SMILES: *C=C]

In some related embodiments, $R_4$ has the following structure:

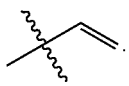

In some other more specific embodiments, $R_3$ and $R_4$ have the following structure:

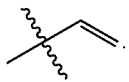

Meanwhile, in one non-limiting embodiment, in Formula 1, each of $L_1$, $L_2$, $L_3$, and $L_4$, which are linkers, may each be independently an aromatic linker.

In particular, in Formula 1, $L_1$, $L_2$, $L_3$, and $L_4$ may each be independently selected from the group consisting of a substituted or unsubstituted phenylene group, a substituted or unsubstituted biphenylene group, a substituted or unsubstituted terphenylene group, a substituted or unsubstituted tetraphenylene group, a substituted or unsubstituted indenylene group, a substituted or unsubstituted naphthylene group, a substituted or unsubstituted azulenylene group, a substituted or unsubstituted indacenylene group, a substituted or unsubstituted acenaphthylene group, a substituted or unsubstituted fluorenylene group, a substituted or unsubstituted spiro-fluorenylene group, a substituted or unsubstituted phenalenylene group, a substituted or unsubstituted phenanthrenylene group, a substituted or unsubstituted anthracenylene group, a substituted or unsubstituted fluoranthrenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted imidazolylene group, a substituted or unsubstituted pyrazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted isoindolylene group, a substituted or unsubstituted indolylene group, a substituted or unsubstituted indazolylene group, a substituted or unsubstituted purinylene group, a substituted or unsubstituted quinolinylene group, a substituted or unsubstituted isoquinolinylene group, a substituted or unsubstituted benzoquinolinylene group, a substituted or unsubstituted phthalazinylene group, a substituted or unsubstituted naphthyridinylene group, a substituted or unsubstituted quinoxalinylene group, a substituted or unsubstituted quinazolinylene group, a substituted or unsubstituted benzoquinolinylene group, a substituted or unsubstituted benzoisoquinolinylene group, a substituted or unsubstituted benzoquinazolinylene group, a substituted or unsubstituted benzoquinoxalinylene group, a substituted or unsubstituted cinnolinylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzoxazolylene group, a substituted or unsubstituted benzimidazolylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted thiazolylene group, a substituted or unsubstituted isothiazolylene group, a substituted or unsubstituted benzothiazolylene group, a substituted or unsubstituted isoxazolylene group, a substituted or unsubstituted oxazolylene group, a substituted or unsubstituted triazolylene group, a substituted or unsubstituted tetrazolylene group, a substituted or unsubstituted oxadiazolylene group, a substituted or unsubstituted triazinylene group, a substituted or unsubstituted dibenzofuranylene group, a substituted or unsubstituted dibenzothiophenylene group, a substituted or unsubstituted carbazolylene group, a substituted or unsubstituted benzocarbazolylene group, a substituted or unsubstituted dibenzocarbazolylene group, a substituted or unsubstituted indolocarbazolylene group, a substituted or unsubstituted indenocarbazolylene group, a substituted or unsubstituted imidazopyrimidinylene group, and a substituted or unsubstituted imidazopyridinylene group.

In certain embodiments related to the foregoing, a and b are both 0. In other specific embodiments, a is 1 and $L_1$ has the following structure:

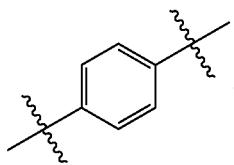

In still other embodiments, b is 1 and $L_2$ has the following structure:

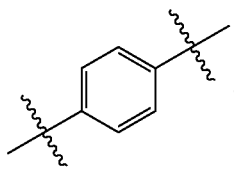

In some embodiments, c and d are both 1. In other specific embodiments, c is 1 and $L_3$ has the following structure:

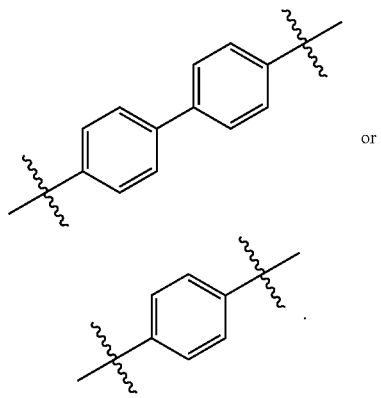

or

In other specific embodiments, d is 1 and $L_4$ has one of the following structures:

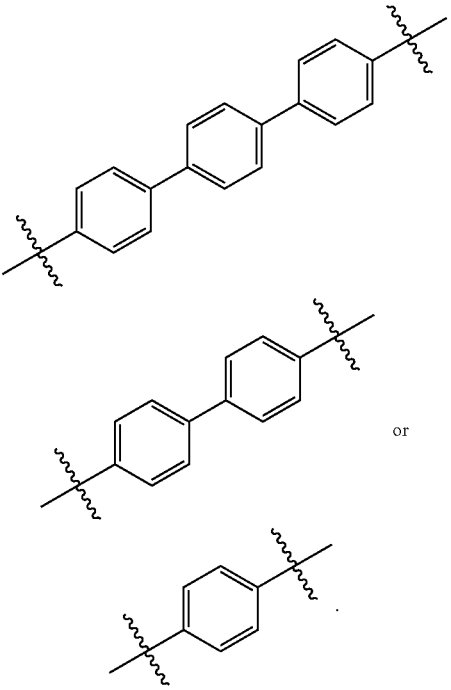

or

In this regard, when the number of aromatic rings constituting $R_1$, $R_2$, $L_1$, $L_2$, $L_3$, and $L_4$ used as linkers increases, a conjugated structure in the entire organic compound becomes excessively long, and thus a bandgap of the organic compound may be excessively reduced. Thus, the number of aromatic rings constituting $R_1$, $R_2$, $L_1$, $L_2$, $L_3$, and $L_4$ may be preferably 1 to 2, more preferably 1. In addition, with regard to hole injection and transport properties, each of $R_1$, $R_2$, $L_1$, $L_2$, $L_3$, and $L_4$ may be independently a 5-membered ring to a 7-membered ring, and particularly may be a 6-membered ring. For example, each of $R_1$ and $R_2$ may be independently a substituted or unsubstituted phenyl group, a substituted or unsubstituted biphenyl group, a substituted or unsubstituted pyrrolyl group, a substituted or unsubstituted imidazole group, a substituted or unsubstituted pyrazole group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted furanyl group, or a substituted or unsubstituted thiophenyl group. In addition, each of $L_1$, $L_2$, $L_3$, and $L_4$ may be independently substituted or unsubstituted phenylene group, a substituted or unsubstituted biphenylene group, a substituted or unsubstituted pyrrolylene group, a substituted or unsubstituted imidazolylene group, a substituted or unsubstituted pyrazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted furanylene group, or a substituted or unsubstituted thiophenylene group.

The organic compound of Formula 1 has, as a core, a fused aromatic moiety of a dibenzothiophene structure, and thus may have excellent thermal stability and a high triplet energy level $T_1$. In addition, the organic compound exhibits excellent hole transfer properties due to amino groups linked to aromatic rings on opposite sides of the dibenzothiophene core. In addition, due to the vinyl group, which has an ethylenic double bond, the organic compound may be cured by a process such as thermal curing, photocuring, or the like, thereby forming crosslinks.

In the organic compound of Formula 1, the linkers ($L_3$ and $L_4$) are attached to a nitrogen and substituted with a $R_3$ and $R_4$, respectively. $R_3$ and $R_4$ are each independently $C_2$-$C_5$ alkenyl (e.g., vinyl group), which is a curable functional group. Thus, when the organic compound of Formula 1 is applied onto an appropriate base, e.g., a hole transfer layer adjacent to an emitting material layer and subjected to curing, the organic compound of Formula 1 is cured while forming crosslinks. For example, to cure the organic compound of Formula 1, thermal curing (e.g., approximately 150° C. to 250° C.) or photocuring using ultraviolet (UV) rays or the like may be performed. The curing process may include the use of an initiator (e.g., a peroxide), which can be used to initiate a radical chain reaction. The process of curing is allowed to continue until a desired molecular weight (i.e., an average molecular weight) is reached.

Since a cured product of the organic compound of Formula 1 forms rigid crosslinks, when the cured product is applied to a hole transfer layer adjacent to an emitting material layer, mixing of a luminescent material constituting the emitting material layer to which a solution process is applied and a hole transferring material constituting other hole transfer layers may be prevented. An interface between the emitting material layer and a neighboring hole transfer layer has a smooth cross-section, and thus overall morphological characteristics of a light-emitting diode including the emissive layer are enhanced.

Holes and electrons may be injected in balance into an emitting material layer over the entire region of a light-emitting diode. Thus, when the cured product of the organic compound of Formula 1 is applied to a light-emitting diode, holes and electrons respectively injected from an anode and a cathode may be injected in balance into the emitting material layer without loss thereof, thereby forming effective excitons, and efficient luminescence may be realized over the entire region of the emitting material layer. Accordingly, a light-emitting diode having enhanced luminous efficiency and capable of operating at a low voltage may be manufactured using the organic compound of Formula 1.

According to one exemplary embodiment, in Formula 1, each of $R_1$, $R_2$, $L_1$, $L_2$, $L_3$, and $L_4$ may be independently an aromatic ring. For example, in Formula 1, when each of $R_1$ and $R_2$ is independently an unsubstituted or substituted $C_5$-$C_{30}$ aryl group or an unsubstituted or substituted $C_4$-$C_{30}$ heteroaryl group, and each of $L_1$, $L_2$, $L_3$, and $L_4$ are each independently an unsubstituted or substituted $C_5$-$C_{30}$ arylene group or an unsubstituted or substituted $C_4$-$C_{30}$ heteroarylene group, the organic compound of Formula 1 overall has an appropriately conjugated structure. Accordingly, the organic compound of Formula 1 may have enhanced hole transfer properties and thus may exhibit maximized luminous efficiency.

More particularly, the organic compound that may be used in a hole transfer layer of a light-emitting diode may include any one of organic compounds represented by Formula 2 below.

Formula 2

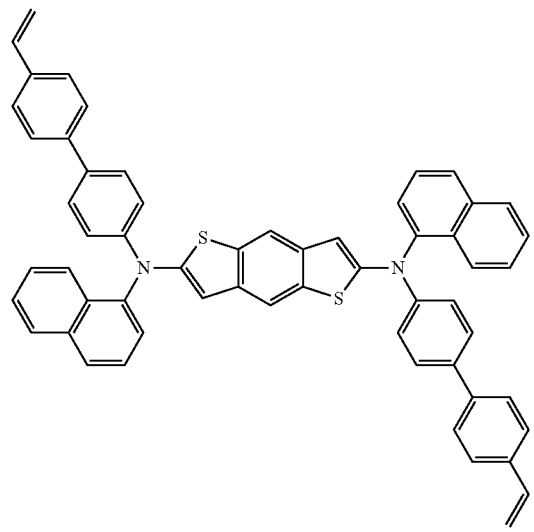

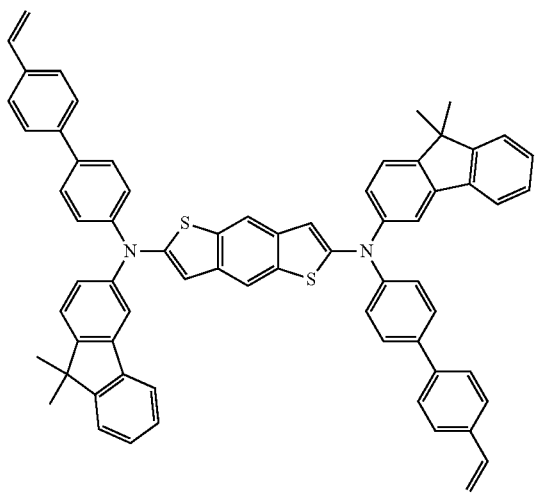

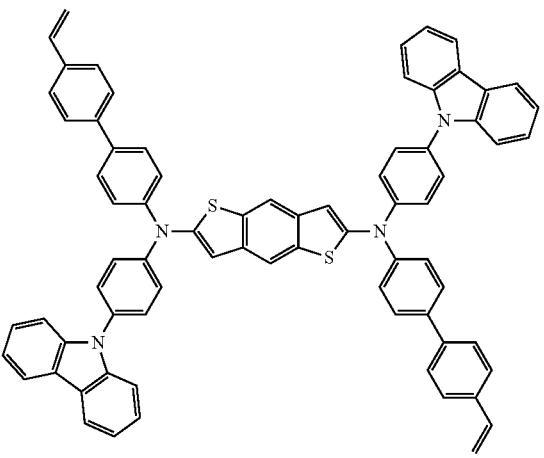

13
-continued
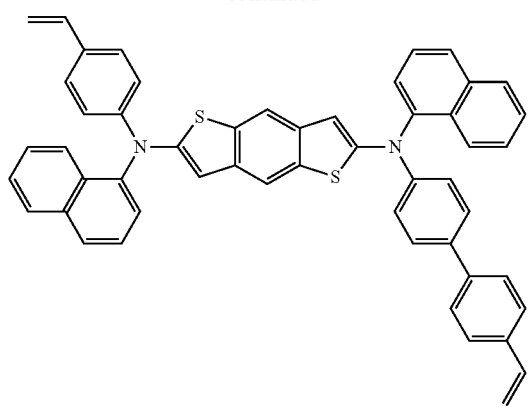
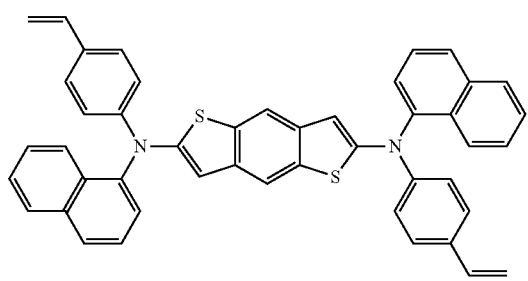
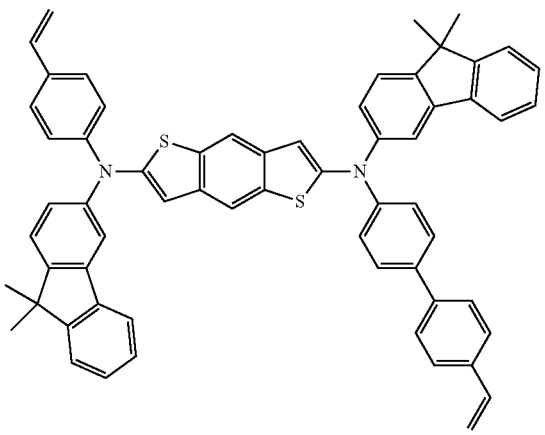
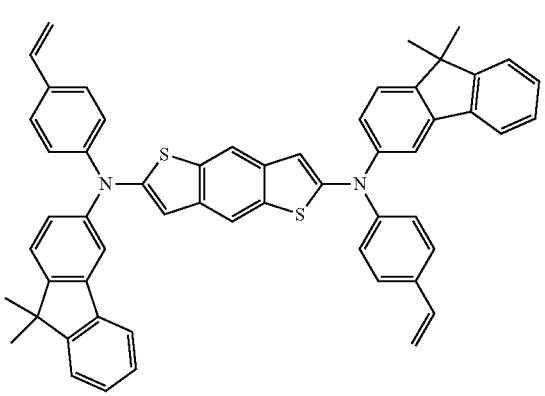
14
-continued
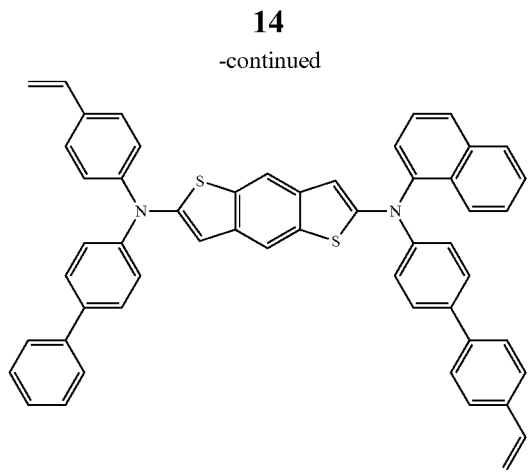
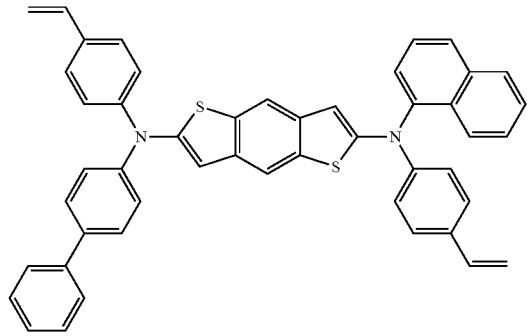
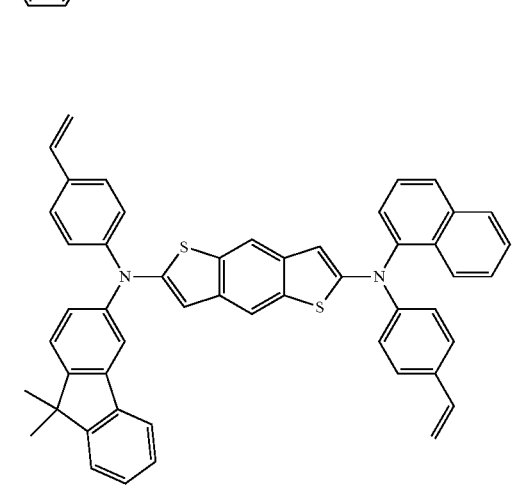
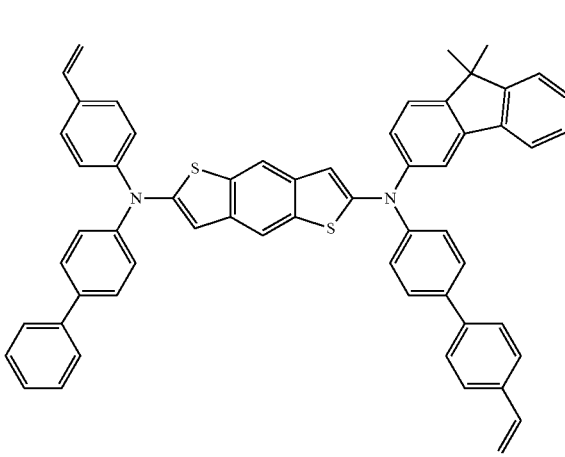

-continued
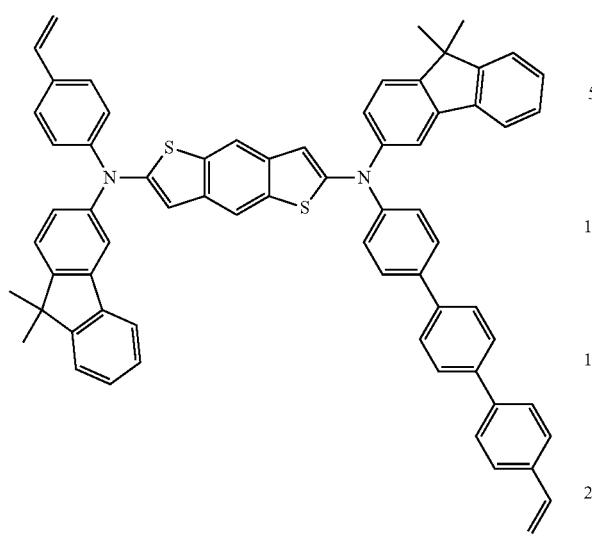
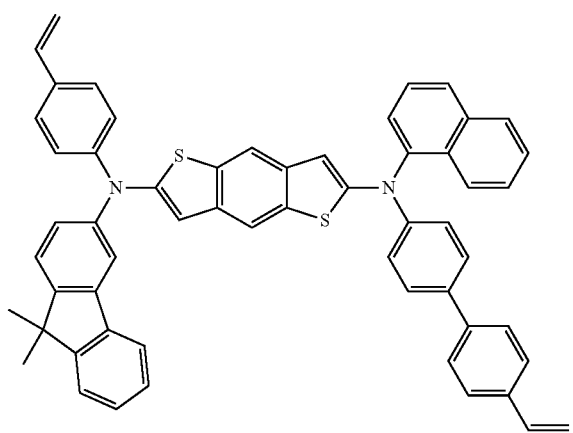
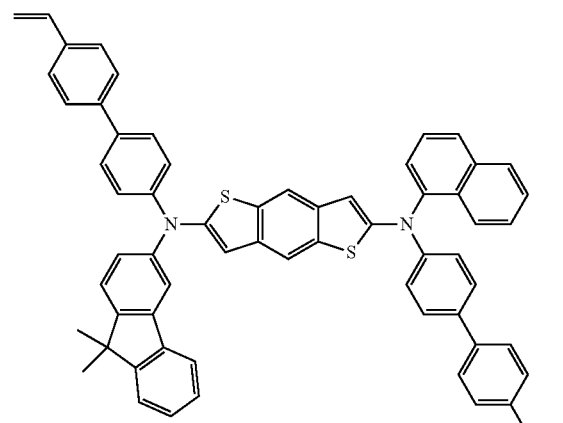
-continued
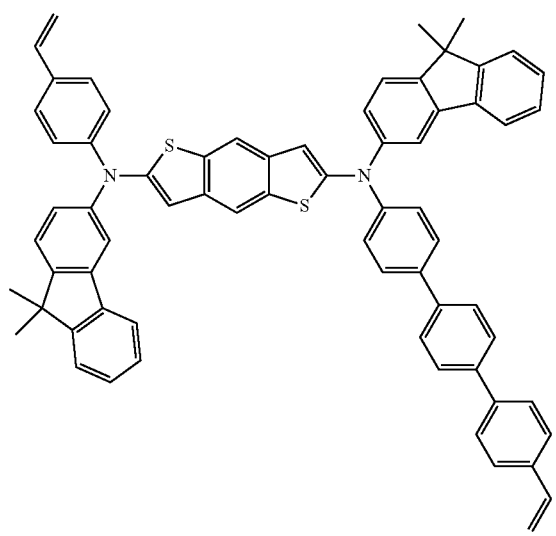
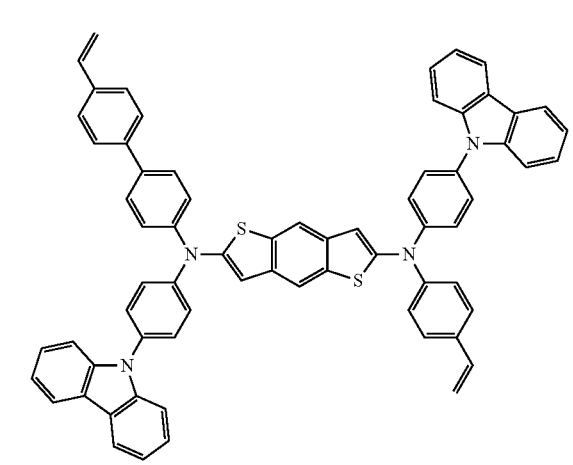
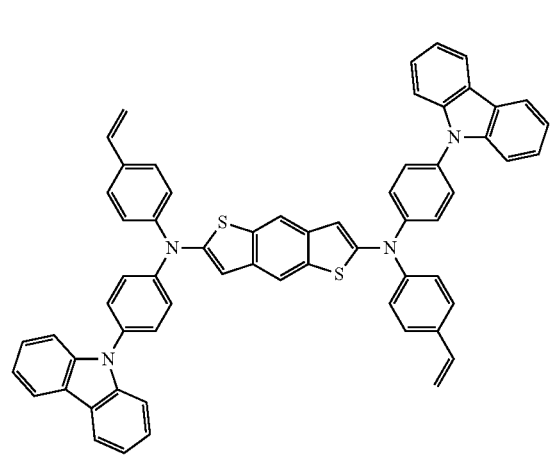

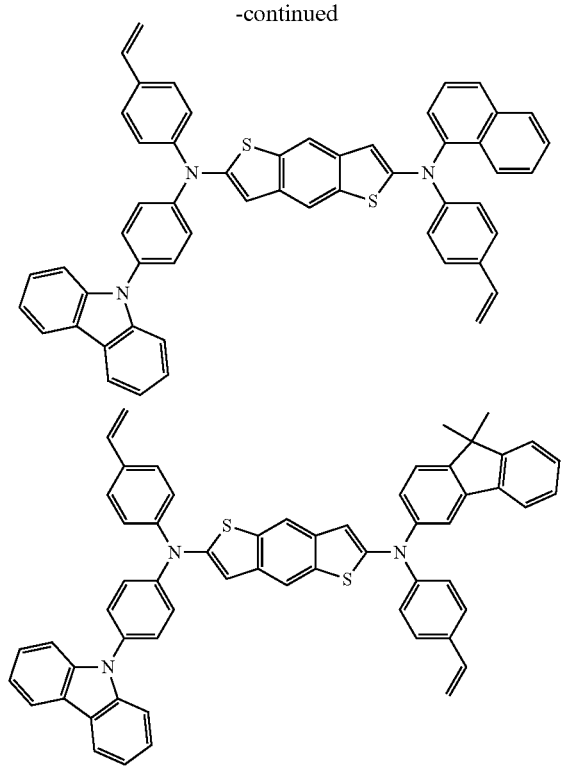

The organic compound of Formula 2 has a dibenzothiophene core with excellent thermal stability and an arylamino group with good hole transfer properties, and has a vinyl group capable of forming crosslinks by curing. Since a cured product of any one of the organic compounds of Formula 2 may form rigid crosslinks, when the cured product is applied to a hole transfer layer adjacent to an emitting material layer, mixing of materials constituting the emitting material layer and a hole transfer layer, which are formed through a solution process, may be prevented. An interface between neighboring emissive layers including the emitting material layer is clearly distinguished and has a smooth cross-sectional shape, and thus the interface between neighboring emissive layers of a light-emitting diode does not have a rough cross-section and the light-emitting diode has excellent overall morphological characteristics. Since holes and electrons are injected in balance into the emitting material layer over the entire region of a light-emitting diode, the light-emitting diode may have enhanced luminous efficiency and a reduced driving voltage, thus reducing power consumption.

Figure 2:
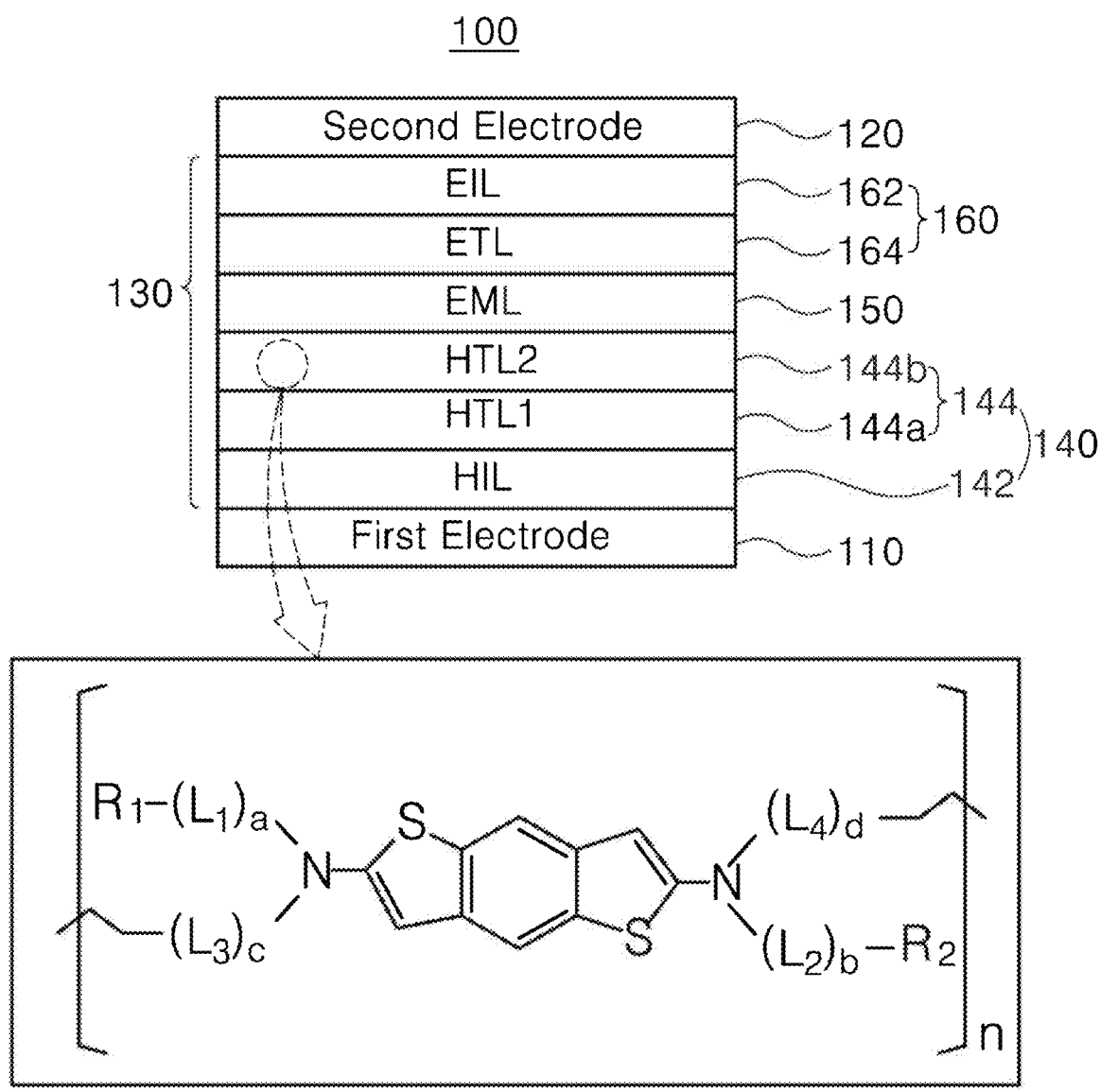
FIG. 2 is a schematic cross-sectional view of a light-emitting diode having a normal structure according to a first exemplary embodiment of the present disclosure.
Figure 3:
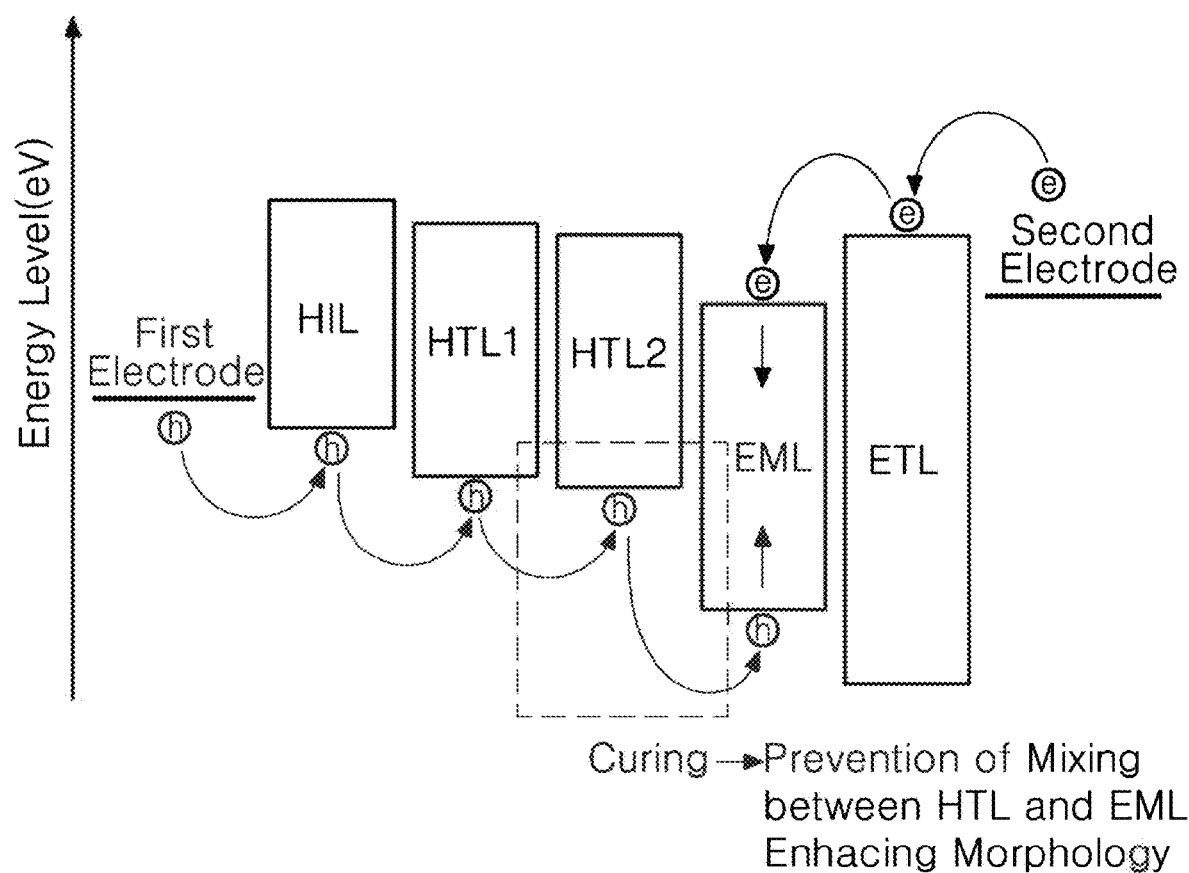
FIG. 3 is a schematic diagram illustrating energy levels of materials constituting electrodes and an emissive layer of the light-emitting diode according to a first exemplary embodiment of the present disclosure, and schematically illustrates that materials constituting the HTL and the EML are not mixed with each other by applying a cured product of an organic compound according to the present disclosure to an HTL2 between an HTL1 and the EML.

Hereinafter, a light-emitting diode including the organic compound according to the present disclosure will be described. FIG. 2 is a schematic cross-sectional view of a light-emitting diode 100 having a normal structure according to a first exemplary embodiment of the present disclosure. FIG. 3 is a schematic diagram illustrating bandgap energy levels of materials constituting electrodes and an emissive layer of the light-emitting diode 100 according to a first exemplary embodiment of the present disclosure.

As illustrated in FIG. 2, the light-emitting diode 100 according to an exemplary embodiment of the present disclosure includes a first electrode 110, a second electrode 120 facing the first electrode 110, and an emissive layer 130 disposed between the first electrode 110 and the second electrode 120 and including an emitting material layer (EML) 150. For example, the emissive layer 130 may further include a first charge transfer layer 140 disposed between the first electrode 110 and the EML 150, and a second charge transfer layer 160 disposed between the EML 150 and the second electrode 120.

In the first embodiment of the present disclosure, the first electrode 110 may be an anode such as a hole injection electrode. The first electrode 110 may be provided on a substrate (not shown in FIG. 2) that may be made of glass or a polymer. For example, the first electrode 110 may be made of a doped or undoped metal oxide selected from indium-tin-oxide (ITO), indium-zinc-oxide (IZO), indium-tin-zinc-oxide (ITZO), indium-copper-oxide (ICO), a tin oxide ($SnO_2$), an indium oxide ($In_2O_3$), cadmium: zinc oxide (Cd: ZnO), fluorine: tin oxide (F:$SnO_2$), indium: tin oxide (In: $SnO_2$), gallium: tin oxide (Ga: $SnO_2$), and aluminum: zinc oxide (Al:ZnO; AZO). Optionally, the first electrode 110 may be made of a metal or non-metal material including nickel (Ni), platinum (Pt), gold (Au), silver (Ag), iridium (Ir), or carbon nanotubes (CNTs), other than the above-described metal oxides.

In the first embodiment of the present disclosure, the second electrode 120 may be a cathode such as an electron injection electrode. For example, the second electrode 120 may be made of Ca, Ba, Ca/Al, LiF/Ca, LiF/Al, $BaF_2$/Al, CsF/Al, $CaCO_3$/Al, $BaF_2$/Ca/Al, Al, Mg, Au:Mg, or Ag:Mg. For example, the first electrode 110 and the second electrode 120 may be stacked with a thickness of about 30 nm to about 300 nm.

In one exemplary embodiment, when the light-emitting diode is of a bottom-emission type, the first electrode 110 may be made of a transparent conductive metal such as ITO, IZO, ITZO, or AZO, and for the second electrode 120, Ca, Ba, Ca/Al, LiF/Ca, LiF/Al, $BaF_2$/Al, Al, Mg, an Ag:Mg alloy, or the like may be used.

The first charge transfer layer 140 capable of constituting the emissive layer 130 is disposed between the first electrode 110 and the EML 150. In the first embodiment of the present disclosure, the first charge transfer layer 140 may be a hole transfer layer configured to supply holes to the EML 150. For example, the first charge transfer layer 140 includes a hole injection layer (HIL) 142 and a hole transport layer (HTL) 144 between the first electrode 110 and the EML 150 such that the HIL 142 is disposed adjacent to the first electrode 110 and the HTL 144 is disposed adjacent to the EML 150.

The HIL 142 facilitates injection of holes from the first electrode 110 into the EML 150. For example, the HIL 142 may be formed of an organic material selected from the group consisting of poly(ethylenedioxythiophene):polystyrenesulfonate (PEDOT:PSS), tetrafluoro-tetracyano-quinodimethane ($F_4$-TCNQ)-doped 4,4',4"-tris(diphenylamino)triphenylamine (TDATA), p-doped phthalocyanine such as $F_4$-TCNQ-doped zinc phthalocyanine (ZnPc), $F_4$-TCNQ-doped N,N'-diphenyl-N,N'-bis(1-naphthyl)-1,1'-biphenyl-4,4"-diamine (α-NPD), hexaazatriphenylene-hexanitrile (HAT-CN), and a combination thereof, but the present disclosure is not limited thereto. For example, a dopant such as $F_4$-TCNQ may be doped in an amount of about 1 wt % to about 30 wt % with respect to the weight of a host. The HIL 142 may be omitted according to the structure and type of the light-emitting diode 100.

The HTL 144 transports holes from the first electrode 110 to the EML 150. In the drawings, although the first charge transfer layer 140 is illustrated as including the HIL 142 and the HTL 144, the first charge transfer layer 140 may be formed as a single layer. For example, the HIL 142 may be omitted and the first charge transfer layer 140 may be formed only of the HTL 144.

In one exemplary embodiment, the HTL 144 may include a cured product of the organic compound of Formula 1 or 2. For example, the cured product of the organic compound of Formula 1, as a cured product of an organic compound that may be applied to the HTL 144, may be represented by Formula 3 below:

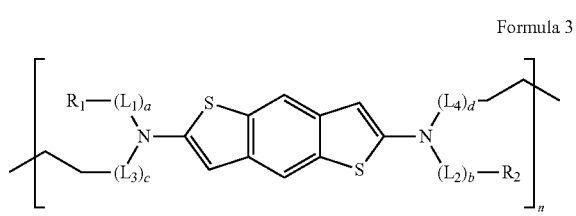

Formula 3 wherein each of $R_1$, $R_2$, $L_1$, $L_2$, $L_3$, $L_4$, a, b, c, and d is the same as defined in Formula 1; and n is an integer of 1 or more. In some embodiments, n ranges from 1 to 10,000. In some embodiments, n ranges from 1 to 5,000. In some embodiments, n ranges from 100 to 5,000.

In one specific embodiment of Formula 3, $R_1$ has one of the following structures:

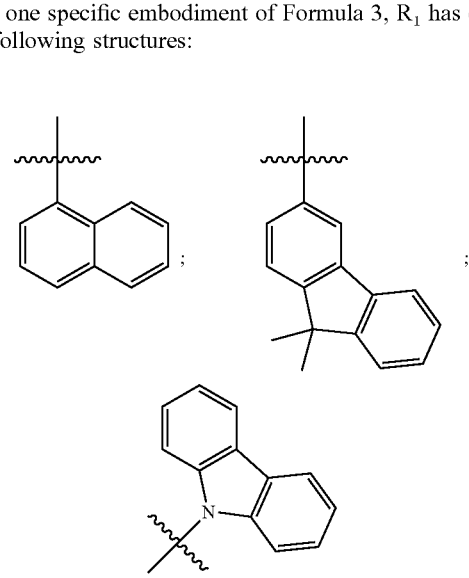

and
$R_2$ has one of the following structures:

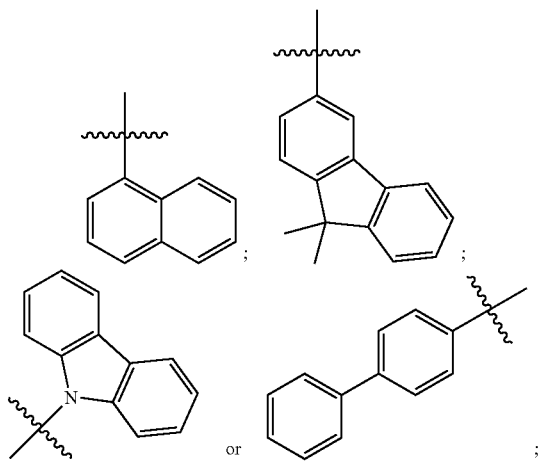

In another related embodiment, c and d are each 1 and $L_3$ has one the following structures:

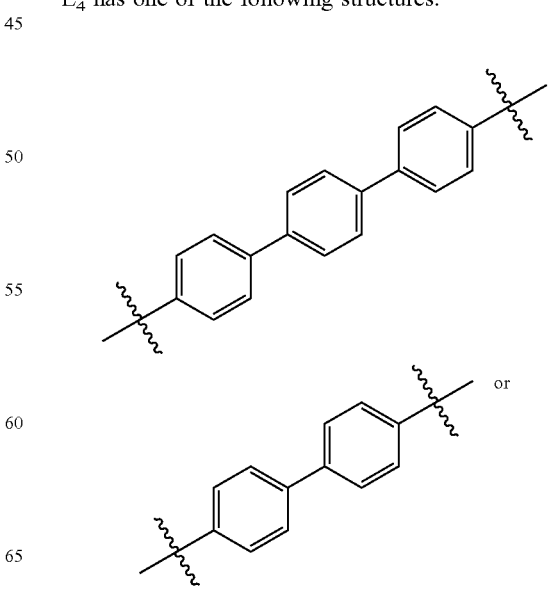

and
$L_4$ has one of the following structures:

-continued

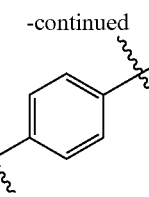

One embodiment provides a light-emitting diode including the compound according to the foregoing embodiments, wherein the light-emitting diode further comprises a hole injection layer, a hole transport layer, an emitting material layer, an electron transport layer, an electron injection layer, a first electrode and a second electrode, wherein the compound is interposed between a surface of the emitting material layer and a surface of the hole transport layer.

In one exemplary embodiment, in the HTL 144, the cured product of the organic compound of Formula 1 or 2 may be used in combination with other hole transporting materials. In this regard, the other hole transporting materials that may be applied to the HTL 144 are not particularly limited, but may be organic materials having excellent hole mobility, prepared by a solution process, and having a triarylamine moiety. For example, other hole transporting materials that may be used in the HTL 144 may include any one of organic materials represented by Formulae 4 to 6 below:

Formula 4

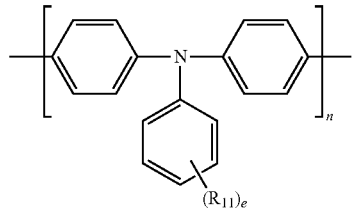

Formula 5

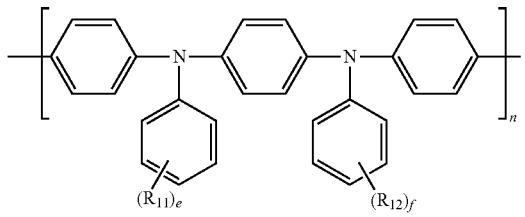

Formula 6

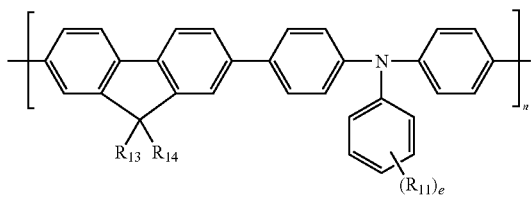

Wherein each of $R_{11}$ to $R_{14}$ is independently an unsubstituted or substituted linear or branched $C_1$-$C_{20}$ alkyl group, an unsubstituted or substituted $C_1$-$C_{20}$ alkoxy group, an unsubstituted or substituted $C_5$-$C_{30}$ aryl group, or an unsubstituted or substituted $C_4$-$C_{30}$ heteroaryl group; each of e and f is independently an integer of 1 to 4; and n is an integer of 1 or more.

In this regard, the cured product of the organic compound of Formula 1 or 2 may be used as a dopant of the HTL 144, and the hole transporting material of one of Formulae 4 to 6 may be used as a host of the HTL 144. In a case in which the HTL 144 consists of a host and a dopant, the cured product of the organic compound of Formula 1 or 2 may be added in an amount of about 1 part by weight to about 200 parts by weight, preferably about 10 parts by weight to about 200 parts by weight, with respect to 100 parts by weight of the host, but the present disclosure is not limited thereto.

In an exemplary embodiment, in Formulae 4 to 6, $R_{11}$ to $R_{14}$ are each independently an unsubstituted or substituted linear or branched $C_1$-$C_{20}$ alkyl group. Examples of the organic compounds of Formulae 4 to 6 include, but are not limited to, poly[N,N'-bis(4-butylphenyl)-N,N'-bis(phenyl)-benzidine] (poly-TPD; p-TPD), poly[(9,9-dioctylfluorenyl-2,7-diyl)-co-(4,4'-(N-(4-sec-butylphenyl)diphenylamine)] (TFB), poly[(9,9-dioctylfluorenyl-2,7-diyl)-co-(4,4'-(N-(p-butylphenyl)diphenylamine))], poly[bis(4-phenyl)(2,4,6-trimethylphenyl)amine] (PTAA), N,N'-bis(3-methylphenyl)-N,N'-bis(phenyl)benzidine (TPD), N,N'-bis(4-methylphenyl)-N,N'-bis(phenyl)benzidine), $N^1,N^4$-diphenyl-$N^1,N^4$-di-m-tolylbenzene-1,4-diamine (TTP), N,N,N',N'-tetra(3-methylphenyl)3,3'-dimethylbenzidien (HMTPD), di-[4-(N,N'-di-p-tolyl-amino)-phenyl]cyclohexane (TAPC), N4,N4'-Bis(4-(6-((3-ethyloxetan-3-yl)methoxy)hexyl)phenyl)-N4,N4'-diphenylbiphenyl-4,4'-diamine (OTPD), and 4,4',4''-tris(N,N-phenyl-3-methylphenylamino)triphenylamine.

In this regard, in the HTL 144, a polymer may be used as a host and the cured product of the organic compound of Formula 1 or 2 may be used as a dopant. In this case, hole mobility of the HTL 144 may be enhanced.

In another exemplary embodiment, the HTL 144 may include a first HTL (HTL1) 144a between the HIL 142 and the EML 150 such that the HTL1 144a is disposed adjacent to the HIL 142, and a second HTL (HTL2) 144b between the HTL1 144a and the EML 150. In this regard, a cured product of the organic compound of Formula 1 or 2, e.g., the cured product of Formula 3, may be applied to the HTL2 144b, and the hole transporting material of one of Formulae 4 to 6 may be applied to the HTL1 144a.

As illustrated in FIG. 3, in a case in which the HTL2 144b formed of the cured product of the organic compound of Formula 1 or 2 is formed between the HTL1 144a and the EML 150, which may be formed by a solution process, due to the HTL2 144b formed of the cured product of the organic compound of Formula 1 or 2 that forms rigid crosslinks, mixing of the hole transporting material constituting the HTL1 144a and a luminescent material constituting the EML 150 may be prevented even when a solution process is performed.

An interface between the HTL 144 and the EML 150 is clearly formed, and thus has a smooth cross-sectional shape. Accordingly, an interface between a plurality of layers constituting the emissive layer 130 does not have a rough cross-sectional shape, and overall morphological characteristics of the light-emitting diode 100 are enhanced. Since holes and electrons may be injected in balance into the entire region of the EML 150 constituting the light-emitting diode 100, the holes and the electrons may efficiently form excitons in the EML 150 without loss thereof. Accordingly, luminous efficiency of the light-emitting diode 100 may be enhanced, and a high voltage does not need to be applied for effective driving of the light-emitting diode 100, and thus the light-emitting diode 100 that can implement low-voltage driving and has low power consumption may be manufactured.

In one exemplary embodiment, the first charge transfer layer 140 including the HIL 142 and the HTL 144 may be formed using one solution process selected from spin coating, drop coating, dip coating, spray coating, roll coating, flow coating, casting, screen printing, and inkjet printing; or a combination thereof. For example, a thickness of the HIL 142 and the HTL 144 may range from about 10 nm to about 200 nm, preferably about 10 nm to about 100 nm, but the present disclosure is not limited thereto.

Meanwhile, the EML 150 may be formed of inorganic luminescent particles or an organic luminescent material. When the EML 150 is formed of inorganic luminescent particles, the inorganic luminescent particles may be inorganic luminescent nanoparticles such as quantum dots (QDs) or quantum rods (QRs).

QDs or QRs are inorganic particles that emit light while electrons in an unstable state drop from a conduction band to a valence band. These inorganic luminescent nanoparticles have a very high extinction coefficient and exhibit an excellent quantum yield among inorganic particles, and thus emit strong fluorescence. In addition, since a luminescence wavelength varies according to the size of inorganic luminescent nanoparticles, when the size of inorganic luminescent nanoparticles is appropriately adjusted, light in the entire visible light region may be obtained, thus realizing a variety of colors. That is, when inorganic luminescent nanoparticles such as QDs or QRs are used as a luminescent material of the EML 150, color purity of individual pixels may be enhanced, and white light consisting of red (R), green (G), and blue (B) light with high purity may also be realized.

In one exemplary embodiment, the QDs or the QRs may have a single structure. In another exemplary embodiment, the QDs or the QRs may have a heterologous structure including a core and a shell. In this case, the shell may be formed as a single shell or multi-shells.

A growth degree, a crystal structure, and the like of these inorganic luminescent nanoparticles may be adjusted according to the reactivity and injection rate of a reactive precursor constituting a core and/or a shell, the type of ligand, a reaction temperature, and the like, and accordingly, light emission at various wavelengths may be induced by adjusting energy bandgaps.

For example, the QDs or the QRs may have a heterologous structure including: a core provided at a center portion thereof and configured to emit light; and a shell covering a surface of the core to protect the core, and in this case, a surface of the shell may be covered with a ligand component for dispersing the QDs or the QRs in a solvent. For example, the QDs or the QRs may have a type-I core/shell structure, in which the energy bandgap of a component constituting the core is surrounded by the energy bandgap of the shell, which is a luminous structure in which electrons and holes move towards the core and are recombined in the core, and as a result, energy is emitted as light.

In a case in which the QDs or the QRs have a type-I core/shell structure, the core is a portion in which light emission substantially occurs, and the luminescence wavelength of the QDs or the QRs is determined according to the size of core. To achieve a quantum confinement effect, it is necessary for the core to have a size smaller than an exciton Bohr radius according to each material, and have an optical bandgap in the corresponding size.

Meanwhile, the shell of the QDs or the QRs promotes a quantum confinement effect of the core and determines the stability of the QDs or the QRs. Unlike internal atoms, atoms that appear on surfaces of colloidal QDs or QRs having a single structure have lone pair electrons that do not participate in chemical bonding. The energy level of these surface atoms is between a conduction band edge and a valence band edge of the QDs or the QRs, and thus charges may be trapped, resulting in formation of surface defects. Luminous efficiency of the QDs or the QRs may be reduced due to a non-radiative recombination process of excitons which results from the surface defects, and the trapped charges react with external oxygen and a compound and thus may cause modification of a chemical composition of the QDs or the QRs, or electric/optical properties of the QDs or the QRs may be permanently lost.

Thus, in one exemplary embodiment, the QDs or the QRs may have a heterologous structure including a core and a shell. In order for the shell to be efficiently formed on a surface of the core, a lattice constant of a material constituting the shell should be similar to that of a material constituting the core. By covering the surface of the core with the shell, oxidation of the core is prevented and thus chemical stability of the QDs or the QRs may be enhanced, loss of excitons due to surface trapping at the surface of the core may be minimized, and energy loss due to molecular vibration may be prevented, resulting in enhancement of quantum efficiency.

The QDs or the QRs may be semiconductor nanocrystals or metal oxide particles having a quantum confinement effect. For example, the QDs or the QRs may include Groups II-IV, III-V, IV-VI, or I-III-VI compound semiconductor nanocrystals. More particularly, cores and/or shells constituting the QDs or the QRs may be Group II-VI compound semiconductor nanocrystals such as CdS, CdSe, CdTe, ZnS, ZnSe, ZnTe, HgS, HgTe, and/or a combination thereof; Group III-V compound semiconductor nanocrystals such as GaP, GaAs, GaSb, InP, InAs, InSb, and/or a combination thereof; Group IV-VI compound semiconductor nanocrystals such as PbS, PbSe, PbTe, and/or a combination thereof; Group I—III-VI compound semiconductor nanocrystals such as $AgGaS_2$, $AgGaSe_2$, $AgGaTe_2$, $CuInS_2$, $CuInSe_2$, $CuGaS_2$, $CuGaSe_2$, and/or a combination thereof, metal oxide nanoparticles such as ZnO, $TiO_2$, and/or a combination thereof; or core-shell structured nanocrystals such as CdSe/ZnSe, CdSe/ZnS, CdS/ZnSe, CdS/ZnS, ZnSe/ZnS, InP/ZnS, ZnO/MgO, and/or a combination thereof. Semiconductor nanoparticles may be undoped or doped with a rare earth element such as europium (Eu), erbium (Er), terbium (Tb), thulium (Tm), or dysprosium (Dy), or a combination thereof, or may be doped with a transition metal element such as manganese (Mn), copper (Cu), silver (Ag), or aluminum (Al), or a combination thereof.

For example, cores constituting the QDs or the QRs may be selected from the group consisting of ZnSe, ZnTe, CdSe, CdTe, InP, ZnCdS, $Cu_xIn_{1-x}S$, $Cu_xIn_{1-x}Se$, $Ag_xIn_{1-x}S$, and a combination thereof. In addition, shells constituting the QDs or the QRs may be selected from the group consisting of ZnS, GaP, CdS, ZnSe, CdS/ZnS, ZnSe/ZnS, ZnS/ZnSe/CdSe, GaP/ZnS, CdS/CdZnS/ZnS, ZnS/CdSZnS, $Cd_xZn_{1-x}S$, and a combination thereof.

Meanwhile, the QDs may be alloy QDs (e.g., $CdS_xSe_{1-x}$, $CdSe_xTe_{1-x}$, and $Zn_xCd_{1-x}Se$) such as homogeneous alloy QDs or gradient alloy QDs.

In one exemplary embodiment, the EML 150 may include QDs or QRs, which are inorganic luminescent nanoparticles having photoluminescence (PL) emission properties at 440 nm, 530 nm, and 620 nm, and thus the manufacture of a white light-emitting diode is enabled. Optionally, the EML 150 may include QDs or QRs, which are luminescent nanoparticles having any one of a red color, a green color, and a blue color, and may be formed such that the EML 150 individually emits light of any one color.

In other embodiments, the EML 150 may be formed of an organic luminescent material. The organic luminescent material of the EML 150 is not particularly limited as long as it is a generally used organic luminescent material. For example, the EML 150 may be formed of an organic luminescent material that emits red light, green light, and/or blue light, and may include a fluorescent material or a phosphorescent material. In addition, the organic luminescent material of the EML 150 may include a host and a dopant. When the organic luminescent material consists of a host-dopant system, the dopant may be doped in an amount of about 1 wt % to about 50 wt %, preferably about 1 wt % to about 30 wt %, with respect to the weight of the host, but the present disclosure is not limited to the above example.

An organic luminescent material used in the EML 150 is not particularly limited as long as it is a commonly used organic host or organic dopant. In one exemplary embodiment, the EML 150 may be formed of an organic luminescent material suitable for a solution process. In particular, the organic host that may be used in the EML 150 may include a phosphorescent host such as 3-(diphenylphosphoryl)-9-(4-(diphenylphosphoyrl)phenyl)-9H-carbazole (PPO21), 2,7-bis(diphenylphosphoryl)spiro[fluorene-7,11'-benzofluorene] (SPPO21), 9-(3-(9H-carbazol-9-yl)phenyl)-3-(diphenylphosphoryl)-9H-carbazole (mCPP01), 2,8-bis(diphenylphosphoryl)dibenzo[b,d]thiophene (PPT), 2,6-bis(3-(9H-carbazol-9-yl)phenyl)pyridine (26DczPPy), 3,5-bis(3-(9H-carbazol-9-yl)phenyl)pyridine (35DczPPy), 3,5-di(9H-carbazol-9-yl)biphenyl (Ph-MCP), 3-(3-(9H-carbazol-9-yl)phenyl)benzofuro[2,3-b]pyridine (PCz-BFP), 4,4'-bis(3-((4-vinylphenoxy)methyl)-9H-carbazol-9-yl)biphenyl (DV-CBP), or 3,3'-di(9H-pyrido[2,3-b]-indol-9-yl)biphenyl (CvBPCb); and/or a fluorescent host such as 2,7-bis[9,9-di(4-methylphenyl)-fluorene-2-yl]-9,9-di(4-methylphenyl) fluorine (TDAF), 2-[9,9-di(4-methylphenyl)-fluorene-2-yl]-9,9-di(4-methylphenyl)fluorene (BDAF), or 1-(7-(9,9'-bianthracene-10-yl)-9,9-dihexyl-9H-flourene-2-yl)pyrene (BAnF8Pye), but the present disclosure is not limited to the above examples.

The organic dopant that may be used in the EML 150 may be a phosphorescent dopant such as bis(2-benzo[b]thiophene-2-yl-pyridine)(acetylacetonate)iridium(III) (Ir(btp)$_2$(acac)), bis(3,5-difluoro-2-(2-pyridyl)phenyl-(2-carboxypyridyl)iridium(III) (FIrPic), bis(2-phenylpyridine)(acetylacetonate)iridium(III) (Ir(ppy)$_2$(acac)), fac-tris(2-phenylpyridine)iridium(III) (fac-Ir(ppy)$_3$), fac-tris(2-(3-p-xylyl)phenyl)pyridine iridium(III) (TEG), tris[2-p-toyl] pyridine)iridium(III) (Ir(mppy)$_3$), bis(3,5-difluoro-4-cyano-2-(2-pyridyl)phenyl-(2-carboxypyridyl)iridium(III) (FCNIrPic), or tris[2-(4-n-hexylphenyl)quinoline]iridium (III) (Hex-Ir(phq)$_3$); and/or a fluorescent dopant such as 9,10-bis[phenyl(m-tolyl)-amino]anthracene (TPA), 9,10-bis [N,N-di-(p-tolyl)-amino]anthracene (TTPA), or 5,6,11,12-tetraphenylnaphthacene (Rubrene), but the present disclosure is not limited to the above examples.

The EML 150 is formed by applying a solution including an appropriate luminescent material in a solvent onto the first charge transfer layer 140, e.g., the HTL2 144b, and then volatilizing the solvent. In one exemplary embodiment, the EML 150 may be formed by applying a dispersion including a luminescent material in a solvent onto the first charge transfer layer 140 through a solution process, and then volatilizing the solvent. The EML 150 may be formed using one solution process selected from spin coating, drop coating, dip coating, spray coating, roll coating, flow coating, casting, screen printing, and inkjet printing; or a combination thereof.

Meanwhile, the second charge transfer layer 160 is located between the EML 150 and the second electrode 120. In the present embodiment, the second charge transfer layer 160 may be an electron transfer layer that supplies electrons to the EML 150. In one exemplary embodiment, the second charge transfer layer 160 includes an electron injection layer (EIL) 162 between the second electrode 120 and the EML 150 such that the EIL 162 is arranged adjacent to the second electrode 120, and an electron transport layer (ETL) 164 between the second electrode 120 and the EML 150 such that the ETL 164 is arranged adjacent to the EML 150.

The EIL 162 facilitates injection of electrons from the second electrode 120 into the EML 150. For example, the EIL 162 may be formed of a material obtained by doping a metal such as aluminum (Al), cadmium (Cd), cesium (Cs), copper (Cu), gallium (Ga), germanium (Ge), indium (In), or lithium (Li) with fluorine or binding such a metal to fluorine; or a metal oxide such as titanium dioxide ($TiO_2$), zinc oxide (ZnO), zirconium oxide (ZrO), tin oxide ($SnO_2$), tungsten oxide ($WO_3$), or tantalum oxide ($Ta_2O_3$) that is undoped or doped with Al, magnesium (Mg), In, Li, Ga, Cd, Cs, Cu, or the like.

The ETL 164 transports electrons to the EML 150. The ETL 164 may be formed of an inorganic material and/or an organic material. In a case in which the ETL 164 is formed of an inorganic material, the ETL 164 may be formed of an inorganic material selected from the group consisting of metal/non-metal oxides such as titanium dioxide ($TiO_2$), zinc oxide (ZnO), zinc magnesium oxide (ZnMgO), zirconium oxide (ZrO), tin oxide ($SnO_2$), tungsten oxide ($WO_3$), tantalum oxide ($Ta_2O_3$), hafnium oxide ($HfO_3$), aluminum oxide ($Al_2O_3$), zirconium silicon oxide ($ZrSiO_4$), barium titanium oxide ($BaTiO_3$), and barium zirconium oxide ($BaZrO_3$) that are undoped or doped with Al, Mg, In, Li, Ga, Cd, Cs, Cu, or the like; semiconductor particles such as CdS, ZnSe, and ZnS that are undoped or doped with Al, Mg, In, Li, Ga, Cd, Cs, Cu, or the like; a nitride such as $Si_3N_4$; and a combination thereof.

In a case in which the ETL 164 is formed of an organic material, for the ETL 164, an organic material such as an oxazole-based compound, an isoxazole-based compound, a triazole-based compound, an isothiazole-based compound, an oxadiazole-based compound, a thiadiazole-based compound, a phenanthroline-based compound, a perylene-based compound, a benzoxazole-based compound, a benzothiazole-based compound, a benzimidazole-based compound, a triazine-based compound, or an aluminum complex may be used. In particular, an organic material that may constitute the ETL 164 may be selected from the group consisting of 3-(biphenyl-4-yl)-5-(4-tertbutylphenyl)-4-phenyl-4H-1,2,4-triazole (TAZ), 2,9-dimethyl-4,7-diphenyl-1,10-phenanthroline (bathocuproine; BCP), 2,2',2"-(1,3,5-benzinetriyl)-tris (1-phenyl-1-H-benzimidazole) (TPBi), 2-[4-(9,10-di-2-naphthalenyl-2-anthracenyl)phenyl]-1-phenyl-1H-benzimidazole, tris(8-hydroxyquinoline)aluminum ($Alq_3$), bis(2-methyl-8-quninolinato)-4-phenylphenolatealuminum (III) (Balq), bis(2-methyl-quninolinato)(triphenylsiloxy), 8-hydroxy-quinolinato lithium (Liq), bis(2-methyl-quinolinato)(triphenylsiloxy)aluminum (III) (Salq), and a combination thereof, but the present disclosure is not limited to the above examples.

Similar to the first charge transfer layer 140, although FIG. 2 illustrates the second charge transfer layer 160 as two layers including the EIL 162 and the ETL 164, the second charge transfer layer 160 may be formed only as a single layer of the ETL 164. In addition, the second charge transfer layer 160 may be formed as a single layer of the ETL 164 using a blend of an electron-transporting material such as the above-described inorganic materials and cesium carbonate.

The second charge transfer layer 160 including the EIL 162 and/or the ETL 164 may be formed using one solution process selected from spin coating, drop coating, dip coating, spray coating, roll coating, flow coating, casting, screen printing, and inkjet printing; or a combination thereof. For example, the EIL 162 and the ETL 164 may be stacked with a thickness of about 10 nm to about 200 nm, preferably, about 10 nm to about 100 nm.

For example, in a case in which a mixed charge transfer layer (CTL) configured such that the HTL 144 constituting the first charge transfer layer 140 is formed of an organic material and the second charge transfer layer 160 is formed of an inorganic material is introduced, luminescence characteristics of the light-emitting diode 100 may be enhanced.

Meanwhile, in a case in which holes pass through the EML 150 and are transferred to the second electrode 120, or electrons pass through the EML 150 and are transferred to the first electrode 110, the lifespan and efficiency of a device may be reduced. To prevent this, the light-emitting diode 100 according to a first embodiment of the present disclosure may include at least one exciton blocking layer adjacent to the EML 150.

For example, the light-emitting diode 100 according to a first embodiment of the present disclosure may include an electron blocking layer (EBL) capable of controlling and preventing transfer of electrons, between the HTL 144 and the EML 150.

For example, the EBL may be formed of TCTA, tris[4-(diethylamino)phenyl]amine), N-(biphenyl-4-yl)-9,9-dimethyl-N-(4-(9-phenyl-9H-carbazole-3-yl)phenyl)-9H-fluorene-2-amine, tri-p-tolylamine, 1,1-bis(4-(N,N'-di(ptolyl)amino)phenyl)cyclohexane (TAPC), m-MTDATA, 1,3-bis(N-carbazolyl)benzene (mCP), 3,3'-bis(N-carbazolyl)-1,1'-biphenyl (mCBP), Poly-TPD, copper phthalocyanine (CuPc), DNTPD, and/or 1,3,5-tris[4-(diphenylamino)phenyl]benzene (TDAPB).

In addition, a hole blocking layer (HBL) as a second exciton blocking layer is located between the EML 150 and the ETL 164, and thus may prevent transfer of holes between the EML 150 and the ETL 164. In one exemplary embodiment, a material for forming the HBL may be an organic derivative such as an oxadiazole-based compound, a triazole-based compound, a phenanthroline-based compound, a benzoxazole-based compound, a benzothiazole-based compound, a benzimidazole-based compound, a triazine-based compound, or the like that may be used in the ETL 164.

For example, the HBL may be formed of 2,9-dimethyl-4,7-diphenyl-1,10-phenanthroline (BCP), BAlq, Alq$_3$, PBD, spiro-PBD, and/or Liq, which have/has a deeper highest occupied molecular orbital (HOMO) energy level than that of a material used in the EML 150.

As described above, according to the first embodiment of the present disclosure, the HTL 144, e.g., the HTL2 144b, disposed between the first electrode 110 and the EML 150 includes the cured product of the organic compound of Formula 1 or 2. The cured product has excellent thermal stability, excellent hole transfer properties, and a rigid structure through crosslinking. Accordingly, in a case in which the EML 150 and the hole transfer layer 140, e.g., the HTL1 144a, are formed through a solution process, the HTL2 144b to which the cured product of the organic compound according to the present disclosure is applied may be disposed therebetween, and accordingly, mixing of the hole transporting material constituting the HTL1 144a and the luminescent material constituting the EML 150 may be prevented. Since the first charge transfer layer 140 including the HTL 144 is clearly distinguished from the EML 150, an interface between these emissive layers has a smooth cross-sectional structure without curves, and overall morphological characteristics of the light-emitting diode 100 are enhanced. Charges may be injected in balance into the entire region of the light-emitting diode 100, and thus may efficiently form excitons. Accordingly, the light-emitting diode 100 may exhibit enhanced luminous efficiency and enables low-voltage driving, thus reducing power consumption.

Figure 4:
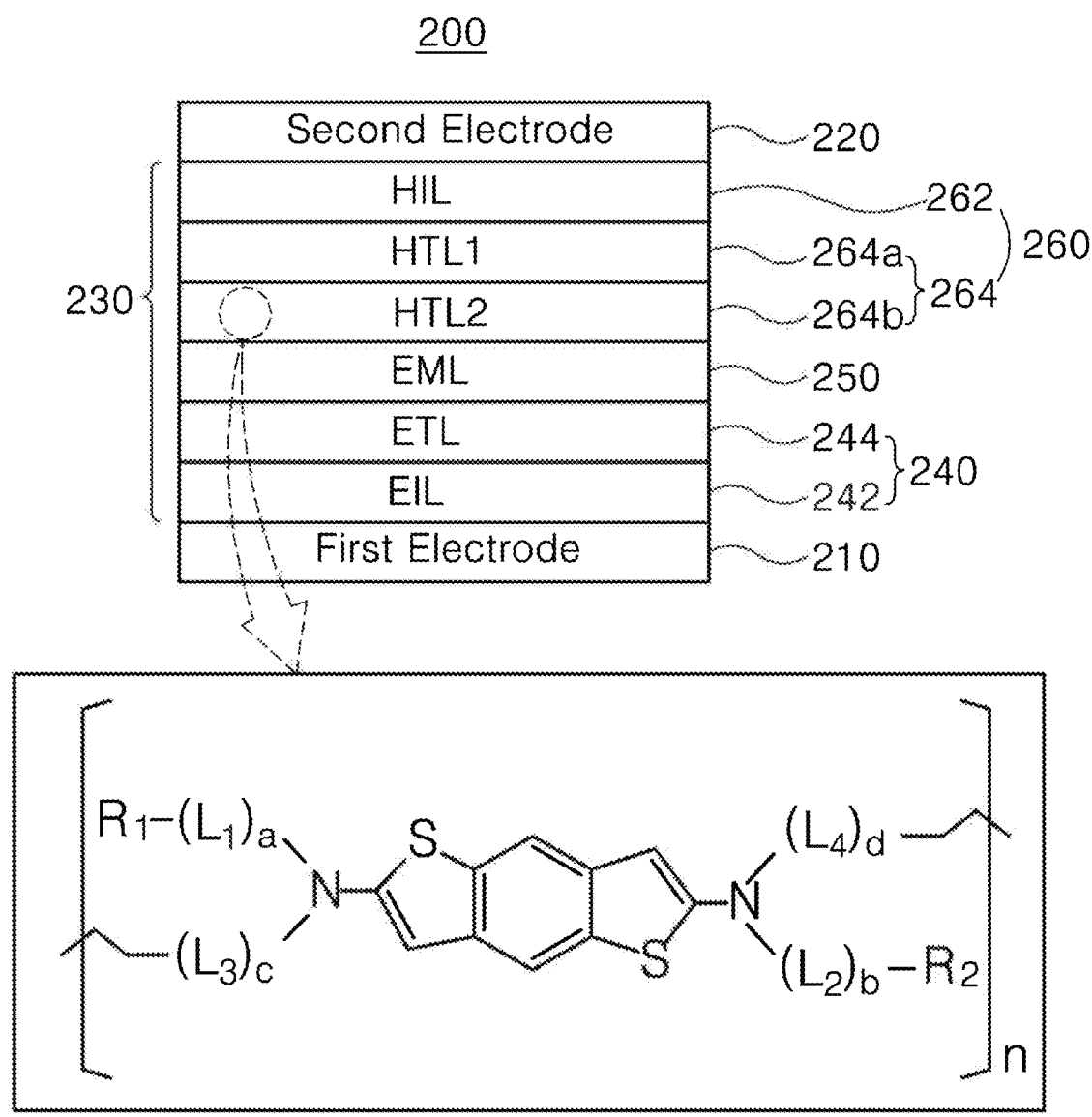
FIG. 4 is a schematic cross-sectional view of a light-emitting diode having an inverted structure according to a second exemplary embodiment of the present disclosure.
Figure 5:
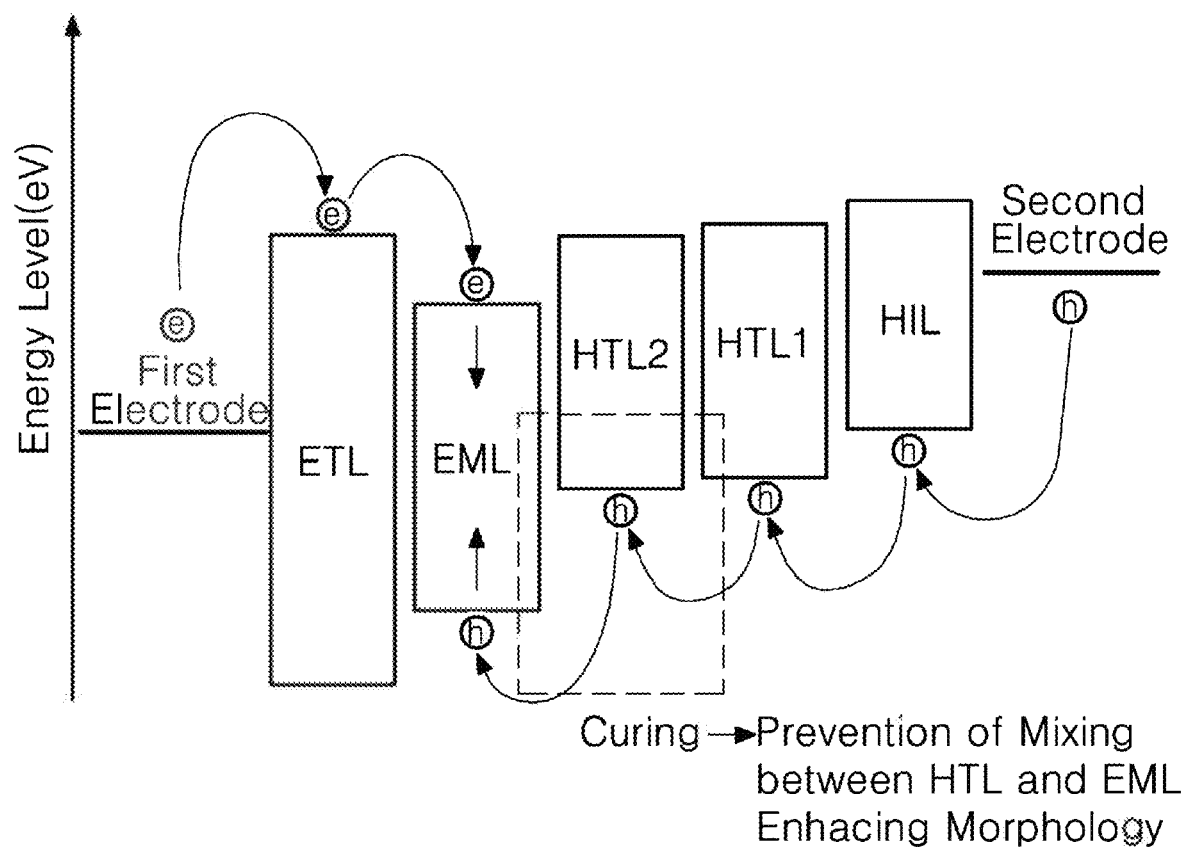
FIG. 5 is a schematic diagram illustrating energy levels of materials constituting electrodes and an emissive layer of the light-emitting diode according to a second exemplary embodiment of the present disclosure, and schematically illustrates that materials constituting an HTL and an EML are not mixed with each other by applying a cured product of an organic compound according to the present disclosure to an HTL2 between an HTL1 and an EML.

Meanwhile, the case of a light-emitting diode having a normal structure such that an HTL is located between a first electrode having a relatively low work function and an EML, and an ETL is located between a second electrode having a relatively high work function and the EML has been described with reference to FIGS. 2 and 3. The light-emitting diode may have an inverted structure, not the normal structure, and this case will be described below. FIG. 4 is a schematic cross-sectional view of a light-emitting diode 200 having an inverted structure according to a second embodiment of the present disclosure. FIG. 5 is a schematic diagram illustrating energy levels of materials constituting electrodes and an emissive layer of the light-emitting diode 200 according to a second embodiment of the present disclosure.

As illustrated in FIG. 4, the light-emitting diode 200 according to a second embodiment of the present disclosure includes a first electrode 210, a second electrode 220 facing the first electrode 210, and an emissive layer 230 disposed between the first electrode 210 and the second electrode 220 and including an EML 250. The emissive layer 230 may further include a first charge transfer layer 240 disposed between the first electrode 210 and the EML 250, and a second charge transfer layer 260 disposed between the second electrode 220 and the EML 250.

In the second embodiment of the present disclosure, the first electrode 210 may be a cathode such as an electron injection electrode. For example, the first electrode 210 may be made of a doped or undoped metal oxide such as ITO, IZO, ITZO, ICO, SnO$_2$, In$_2$O$_3$, Cd:ZnO, F:SnO$_2$, In:SnO$_2$, Ga:SnO$_2$, or AZO; or, other than the above-described metal oxides, a material including nickel (Ni), platinum (Pt), gold (Au), silver (Ag), iridium (Ir), or carbon nanotubes.

In the second embodiment of the present disclosure, the second electrode 220 may be an anode such as a hole injection electrode. For example, the second electrode 220 may be made of Ca, Ba, Ca/Al, LiF/Ca, LiF/Al, BaF$_2$/Al, CsF/Al, CaCO$_3$/Al, BaF$_2$/Ca/Al, Al, Mg, Au:Mg, or Ag:Mg. For example, the first electrode 210 and the second electrode 220 may be stacked with a thickness of about 30 nm to about 300 nm.

In the second embodiment of the present disclosure, the first charge transfer layer 240 may be an electron transfer layer that supplies electrons to the EML 250. In one exemplary embodiment, the first charge transfer layer 240 includes an EIL 242 between the first electrode 210 and the EML 250 such that the EIL 242 is located adjacent to the first electrode 210, and an ETL 244 between the first electrode 210 and the EML 250 such that the ETL 244 is located adjacent to the EML 250.

The EIL 242 may be formed of a material obtained by doping a metal such as Al, Cd, Cs, Cu, Ga, Ge, In, or Li with fluorine or binding such a metal to fluorine; or a metal oxide such as $TiO_2$, ZnO, ZrO, $SnO_2$, $WO_3$, or $Ta_2O_3$ that is undoped or doped with Al, Mg, In, Li, Ga, Cd, Cs, Cu, or the like.

The ETL 244 may be formed of an inorganic material and/or an organic material. In a case in which the ETL 244 is formed of an inorganic material, the ETL 244 may be formed of an inorganic material selected from the group consisting of metal/non-metal oxides such as $TiO_2$, ZnO, ZnMgO, ZrO, $SnO_2$, $WO_3$, $Ta_2O_3$, $HfO_3$, $Al_2O_3$, $ZrSiO_4$, $BaTiO_3$, and $BaZrO_3$ that are undoped or doped with Al, Mg, In, Li, Ga, Cd, Cs, Cu, or the like; semiconductor particles such as CdS, ZnSe, and ZnS that are undoped or doped with Al, Mg, In, Li, Ga, Cd, Cs, Cu, or the like; a nitride such as $Si_3N_4$; and a combination thereof.

In a case in which the ETL 244 is formed of an organic material, for the ETL 244, an oxazole-based compound, an isoxazole-based compound, a triazole-based compound, an isothiazole-based compound, an oxadiazole-based compound, a thiadiazole-based compound, a perylene-based compound, or an aluminum complex may be used. In particular, an organic material that may constitute the ETL 244 may be selected from the group consisting of TAZ, BCP, TPBi, 2-[4-(9,10-di-2-naphthalenyl-2-anthracenyl)phenyl]-1-phenyl-1H-benzimidazole, $Alq_3$, Balq, LIQ, Salq, and a combination thereof, but the present disclosure is not limited to the above examples.

Meanwhile, the first charge transfer layer 240 may be formed only as a single layer of the ETL 244. In addition, the first charge transfer layer 240 may be formed as a single layer of the ETL 244 using a blend of an electron-transporting material such as the above-described inorganic particles and cesium carbonate. For example, the EL 242 and the ETL 244 may be stacked with a thickness of about 10 nm to about 200 nm, preferably about 10 nm to about 100 nm.

The EML 250 may be formed of inorganic luminescent particles or an organic luminescent material. The inorganic luminescent particles may be inorganic luminescent nanoparticles such as QDs or QRs. QDs or QRs may have a single structure, or a heterologous structure including a core/a shell.

The QDs or the QRs may be semiconductor nanocrystals or metal oxide particles having a quantum confinement effect. For example, the QDs or the QRs may include Groups II-IV, III-V, IV-VI, or I-III-VI compound semiconductor nanocrystals. More particularly, cores and/or shells constituting the QDs or the QRs may be Group II-VI compound semiconductor nanocrystals such as CdS, CdSe, CdTe, ZnS, ZnSe, ZnTe, HgS, HgTe, and/or a combination thereof; Group III-V compound semiconductor nanocrystals such as GaP, GaAs, GaSb, InP, InAs, InSb, and/or a combination thereof; Group IV-VI compound semiconductor nanocrystals such as PbS, PbSe, PbTe, and/or a combination thereof; Group I—III-VI compound semiconductor nanocrystals such as $AgGaS_2$, $AgGaSe_2$, $AgGaTe_2$, $CuInS_2$, $CuInSe_2$, $CuGaS_2$, $CuGaSe_2$, and/or a combination thereof, metal oxide nanoparticles such as ZnO, $TiO_2$, and/or a combination thereof; or core-shell structured nanocrystals such as CdSe/ZnSe, CdSe/ZnS, CdS/ZnSe, CdS/ZnS, ZnSe/ZnS, InP/ZnS, ZnO/MgO, and/or a combination thereof. Semiconductor nanoparticles may be undoped or doped with a rare earth element such as Eu, Er, Tb, Tm, or Dy, or a combination thereof, or may be doped with a transition metal element such as Mn, Cu, Ag, or Al, or a combination thereof.

In a case in which the EML 250 is formed of an organic luminescent material, the EML 250 may be formed of an organic luminescent material that emits red light, green light, and/or blue light, and may include a fluorescent material or a phosphorescent material. In addition, the organic luminescent material of the EML 250 may include a host and a dopant. When the organic luminescent material consists of a host-dopant system, the dopant may be doped in an amount of about 1 wt % to about 50 wt %, preferably about 1 wt % to about 30 wt %, with respect to a weight of the host, but the present disclosure is not limited thereto.

The EML 250 is formed by applying a solution including a luminescent material in a solvent onto the first charge transfer layer 240, e.g., the ETL 244, and then volatilizing the solvent.

Meanwhile, in the second embodiment of the present disclosure, the second charge transfer layer 260 may be a hole transfer layer that supplies holes to the EML 250. In one exemplary embodiment, the second charge transfer layer 260 includes a HIL 262 between the second electrode 220 and the EML 250 such that the HIL 262 is located adjacent to the second electrode 220, and an HTL 264 between the second electrode 220 and the EML 250 such that the HTL 264 is located adjacent to the EML 250.

The HIL 262 may be formed of a material selected from the group consisting of PEDOT:PSS, $F_4$-TCNQ-doped TDATA, p-doped phthalocyanine such as $F_4$-TCNQ-doped ZnPc, $F_4$-TCNQ-doped α-NPD, HAT-CN, and a combination thereof, but the present disclosure is not limited to the above examples. For example, a dopant such as $F_4$-TCNQ may be doped in an amount of about 1 wt % to about 30 wt % with respect to the weight of a host. The HIL 262 may be omitted according to the structure and type of the light-emitting diode 200.

The HTL 264 transports holes from the second electrode 220 to the EML 250. The HTL 264 may include a cured product of the organic compound of Formula 1 or 2, for example, the cured product of Formula 3.

In one exemplary embodiment, the HTL 264 may include the cured product of the organic compound of Formula 1 or 2, and the hole transporting material of one of Formulae 4 to 6.

In another exemplary embodiment, the HTL 264 may include a first HTL (HTL1) 264a between the HIL 262 and the EML 250 such that the first HTL 264a is disposed adjacent to the HIL 262, and a second HTL (HTL2) 264b between the HTL1 264a and the EML 250. In this regard, the cured product of the organic compound of Formula 1 or 2, for example, the cured product of Formula 3, may be applied to the HTL2 264b, and the hole transporting material of one of Formulae 4 to 6 may be applied to the HTL1 264a. In this case, as illustrated in FIG. 5, due to the HTL2 264b formed of the cured product of the organic compound of Formula 1 or 2 which forms rigid crosslinks, mixing of the hole transporting material constituting the HTL1 264a and the luminescent material constituting the EML 250 may be prevented even when a solution process is performed.

The second charge transfer layer 260 may be formed as a single layer. For example, the HIL 262 may be omitted and the second charge transfer layer 260 may be formed of only the HTL 264. A thickness of the HIL 262 and the HTL 264 may range from about 10 nm to about 200 nm, preferably about 10 nm to about 100 nm, but the present disclosure is not limited thereto.

Similar to the first embodiment, the light-emitting diode 200 according to a second embodiment of the present disclosure may include at least one exciton blocking layer adjacent to the EML 250. For example, the light-emitting diode 200 may further include an electron blocking layer disposed between the EML 250 and the HTL 264 and capable of controlling and preventing transfer of electrons, and/or a hole blocking layer disposed between the ETL 244 and the EML 250 and capable of controlling and preventing transfer of holes.

For example, the cured product of the organic compound of Formula 1 or 2 forms rigid crosslinks. Thus, when the HTL2 264b is formed of such a cured product, the hole transporting material constituting the HTL1 264a formed by a solution process and the luminescent material constituting the EML 250 cannot be mixed. An interface between the HTL 264 and the EML 250 is clearly distinguished, and an interface between the HTL 264 and the EML 250 has a smooth cross-sectional shape. Accordingly, an interface between a plurality of layers constituting the emissive layer 230 does not have a rough cross-sectional shape, and overall morphological characteristics of the light-emitting diode 200 are enhanced. Since holes and electrons may be injected in balance into the entire region of the EML 250 constituting the light-emitting diode 200, the holes and the electrons may efficiently form excitons in the EML 250 without loss thereof, and the light-emitting diode 200 may exhibit enhanced luminous efficiency and implement low-voltage driving.

Figure 6:
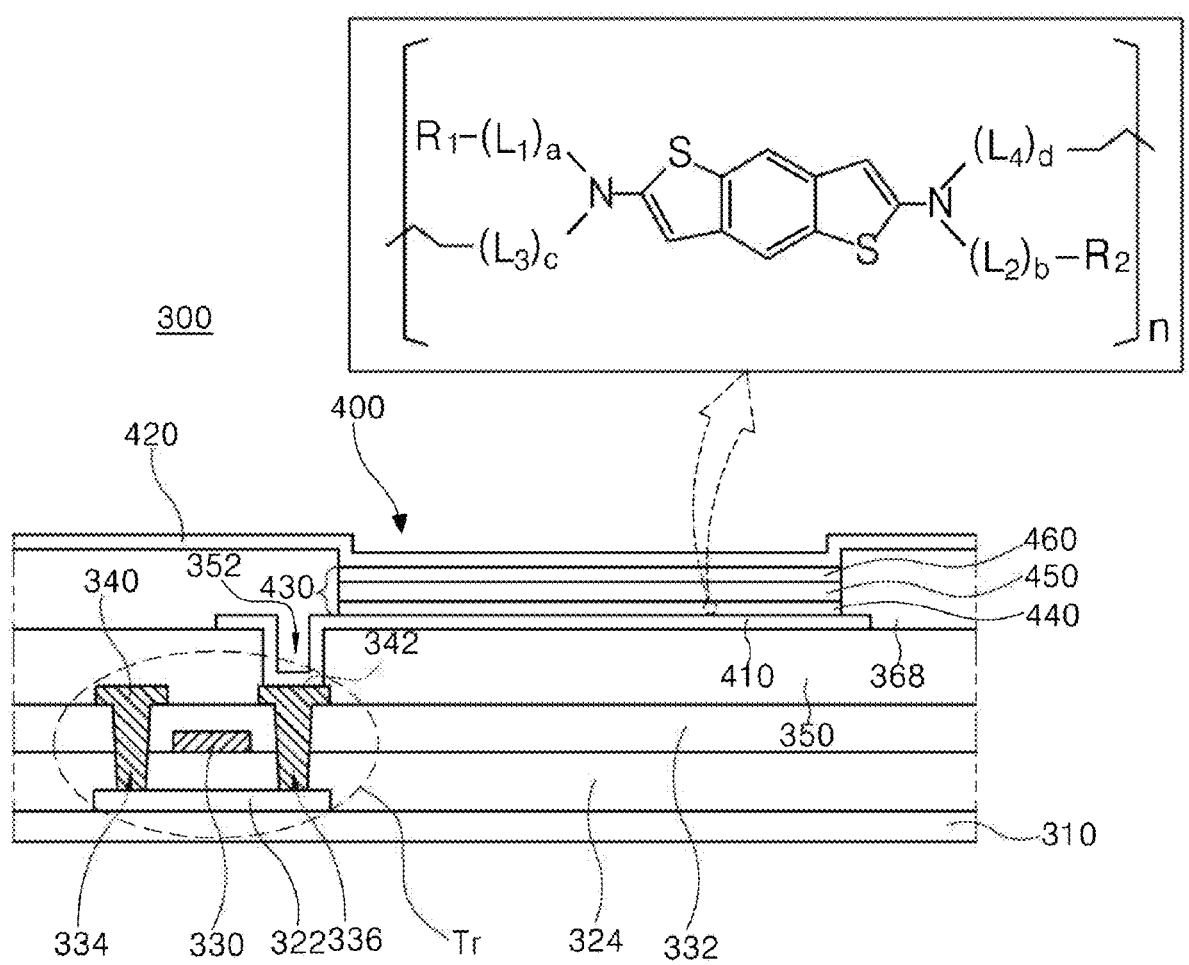
FIG. 6 is a schematic cross-sectional view illustrating a light-emitting diode display device, which is an example of a light-emitting device employing a light-emitting diode according to an exemplary embodiment of the present disclosure.

Thus, a light-emitting diode, in which the cured product of the organic compound of Formula 1 or 2 is applied to a hole transfer layer, may be applied to a lighting device or a light-emitting device such as a display device. For example, a light-emitting device including a light-emitting diode in which the organic compound according to the present disclosure is applied to a hole transfer layer will be described. FIG. 6 is a schematic cross-sectional view illustrating a light-emitting display device 300 according to an exemplary embodiment of the present disclosure.

As illustrated in FIG. 6, the light-emitting display device 300 includes a substrate 310, and, on the substrate 310, a driving thin film transistor Tr, which is a driving element, and a light-emitting diode 400 connected to the driving thin film transistor Tr.

A semiconductor layer 322 formed of an oxide semiconductor material or polycrystalline silicon is provided on the substrate 310. When the semiconductor layer 322 is formed of an oxide semiconductor material, a light-shielding pattern (not shown) may be formed on a lower portion of the semiconductor layer 322, and the light-shielding pattern prevents light from being incident on the semiconductor layer 322, thus preventing the semiconductor layer 322 from being deteriorated by light. Unlike this, the semiconductor layer 322 may be formed of polycrystalline silicon, and in this case, opposite edges of the semiconductor layer 322 may be doped with impurities.

A gate insulating film 324 formed of an insulating material is disposed on the semiconductor layer 322. The gate insulating film 324 may be formed of an inorganic insulating material such as a silicon oxide ($SiO_2$) or a silicon nitride ($SiN_x$). A gate electrode 330 made of a conductive material such as a metal is disposed on the gate insulating film 324 to correspond to a center of the semiconductor layer 322.

An interlayer insulating film 332 formed of an insulating material is disposed on the gate electrode 330. The interlayer insulating film 332 may be formed of an inorganic insulating material such as $SiO_2$ or $SiN_x$, or an organic insulating material such as benzocyclobutene or photo-acryl.

The interlayer insulating film 332 has first and second semiconductor layer contact holes 334 and 336 that expose opposite sides of the semiconductor layer 322. The first and second semiconductor layer contact holes 334 and 336 are located on opposite sides of the gate electrode 330 to be spaced apart from the gate electrode 330. A source electrode 340 and a drain electrode 342, which are formed of a conductive material such as a metal, are disposed on the interlayer insulating film 332.

The source electrode 340 and the drain electrode 342 are spaced apart from each other with respect to the gate electrode 330, and contact opposite sides of the semiconductor layer 322 through the first and second semiconductor contact holes 334 and 336, respectively. The semiconductor layer 322, the gate electrode 330, the source electrode 340, and the drain electrode 342 constitute the driving thin film transistor Tr, which is a driving element.

In FIG. 6, the driving thin film transistor Tr has a coplanar structure in which the gate electrode 330, the source electrode 340, and the drain electrode 342 are disposed on the semiconductor layer 322. Unlike this, the driving thin film transistor Tr may have an inverted staggered structure in which a gate electrode is disposed on a lower portion of a semiconductor layer and a source electrode and a drain electrode are disposed on an upper portion of the semiconductor layer. In this case, the semiconductor layer may be formed of amorphous silicon.

Although not shown, a gate line and a data line cross each other to define a pixel region, and a switching element connected to the gate line and the data line is further formed in the pixel region. The switching element is connected to the driving thin film transistor Tr, which is a driving element. In addition, a power line is parallelly spaced apart from the gate line or the data line, and the driving thin film transistor Tr may further include a storage capacitor configured to constantly maintain a voltage of a gate electrode of the driving thin film transistor Tr, which is a driving element, for one frame.

Meanwhile, a passivation layer 350 having a drain contact hole 352, through which the drain electrode 342 of the driving thin film transistor Tr is exposed, is formed to cover the driving thin film transistor Tr. For example, the passivation layer 350 may be formed of an inorganic insulating material such as $SiO_2$ or $SiN_x$, or an organic insulating material such as benzocyclobutene or photo-acryl.

A first electrode 410 connected to the drain electrode 342 of the driving thin film transistor Tr through the drain contact hole 352 is disposed on the passivation layer 350 in each pixel region. The first electrode 410 may be an anode or a cathode, and may be made of a conductive material having a relatively high work function. For example, the first electrode 410 may be made of a doped or undoped metal oxide such as ITO, IZO, ITZO, ICO, $SnO_2$, $In_2O_3$, Cd:ZnO, $F:SnO_2$, $In:SnO_2$, $Ga:SnO_2$ or AZO, or a metal material including Ni, Pt, Au, Ag, Ir, or carbon nanotubes, other than the above-described metal oxides.

Meanwhile, in a case in which the light-emitting display device 300 of the present disclosure is a top-emission type, a reflective electrode or a reflective layer may be further disposed on a lower portion of the first electrode 410. For example, the reflective electrode or the reflective layer may be formed of an aluminum-palladium-copper (APC) alloy.

In addition, a bank layer 368 is disposed on the passivation layer 350 to cover an edge of the first electrode 410. The bank layer 368 exposes a center of the first electrode 410 to correspond to a pixel region.

An emissive layer 430 is disposed on the first electrode 410. The emissive layer 430 may be formed only as an EML, but may have multiple charge transfer layers to enhance luminous efficiency. For example, FIG. 6 illustrates the emissive layer 430 as including a first charge transfer layer 440, an emitting material layer 450, and a second charge transfer layer 460 that are sequentially stacked between the first electrode 410 and a second electrode 420.

For example, the first charge transfer layer 440 may be a hole transfer layer, and may include the HIL 142 (see FIG. 2) and the HTL 144 (see FIG. 2) that are formed of an organic material. A hole transport layer constituting the first charge transfer layer 440 includes the cured product of the organic compound of Formula 1 or 2. For example, the cured product of the organic compound of Formula 1 or 2 may constitute the HTL2 144b (see FIG. 2) disposed adjacent to the EML 450, and the hole transporting material of one of Formulae 4 to 6 may constitute the HTL1 144a (see FIG. 2).

The emitting material layer 440 may be formed of an inorganic luminescent material or an organic luminescent material. Meanwhile, the second charge transfer layer 450 may be an electron transfer layer, and may consist of the EIL 162 (see FIG. 2) and the ETL 164 (see FIG. 2). For example, the second charge transfer layer 450 may be formed of an inorganic material or an organic material.

The second electrode 420 is disposed above the substrate 310 above which the emissive layer 430 is disposed. The second electrode 420 may be disposed on the entire surface of a display region, may be made of a conductive material having a relatively low work function, and may be a cathode or an anode. For example, the second electrode 420 may be made of Ca, Ba, Ca/Al, LiF/Ca, LiF/Al, BaF$_2$/Al, CsF/Al, CaCO$_3$/Al, BaF$_2$/Ca/Al, Al, Mg, Au:Mg, or Ag:Mg.

FIG. 6 illustrates the light-emitting diode 400 having a normal structure in which the first charge transfer layer 440 as a hole transfer layer is disposed between the first electrode 410 and the emitting material layer 450, and the second charge transfer layer 460 as an electron transfer layer is disposed between the second electrode 420 and the emitting material layer 450.

In another embodiment, a light-emitting diode having an inverted structure in which a first charge transfer layer as an electron transfer layer is disposed between the first electrode 410 and the emitting material layer 450, and a second charge transfer layer as a hole transfer layer is disposed between the second electrode 420 and the emitting material layer 450 may be manufactured. In this case, the cured product of the organic compound of Formula 1 or 2 may be used in a hole transport layer constituting the second charge transfer layer 460 disposed between the second electrode 420 and the emitting material layer 450.

By applying the cured product of the organic compound of Formula 1 or 2 to the first charge transfer layer 440 or the second charge transfer layer 460 that may be a hole transfer layer, mixing of a hole transporting material constituting the hole transfer layer and the luminescent material constituting the EML 450 is prevented even when a solution process is performed. An interface of the emissive layer 430 has a smooth cross-sectional shape (e.g., as measured by TEM), and overall morphological characteristics of the light-emitting diode 400 are enhanced. Since holes and electrons are injected in balance into the EML 450 over the entire region of the light-emitting diode 400, luminous efficiencies of the light-emitting diode 400 and the light-emitting display device 300 including the same may be enhanced, the light-emitting diode 400 may be driven at a low voltage, and the light-emitting diode 400 and the light-emitting display device 300 that have reduced power consumption may be manufactured.

Hereinafter, the present disclosure will be described with reference to the following examples, but is not intended to be limited by the technical spirit described in the examples set forth herein.

Synthesis Example 1: Synthesis of Compound 1

(1) Synthesis of Compound M1

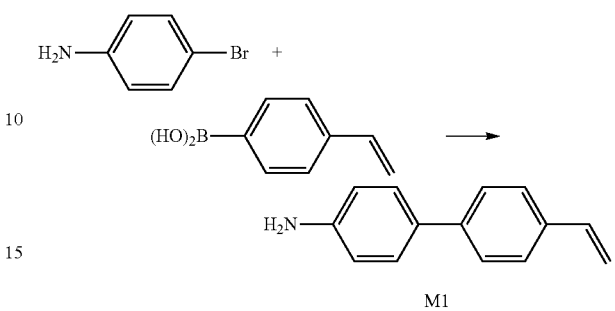

M1

In a 100 ml round-bottom flask, 2.0 g (11.6 mmol) of 4-bromoaniline, 2.6 g (17.4 mmol) of 4-vinylphenylboronic acid, 0.01 g (0.5 mol %) of palladium diacetate, 0.03 g (1.0 mol %) of tricyclohexylphosphine, and 9.3 g (34.8 mmol) of K$_3$PO$_4$·3H$_2$O were dissolved in 45 ml of toluene, and then the resulting solution was stirred in a bath at 80° C. for 10 minutes. When the reaction was completed, the reaction product was cooled to room temperature and extracted with water and ethyl acetate, followed by column separation using dichloromethane and n-hexane, thereby obtaining 1.8 g (9.2 mmol) of Compound M1.

(2) Synthesis of Compound M2

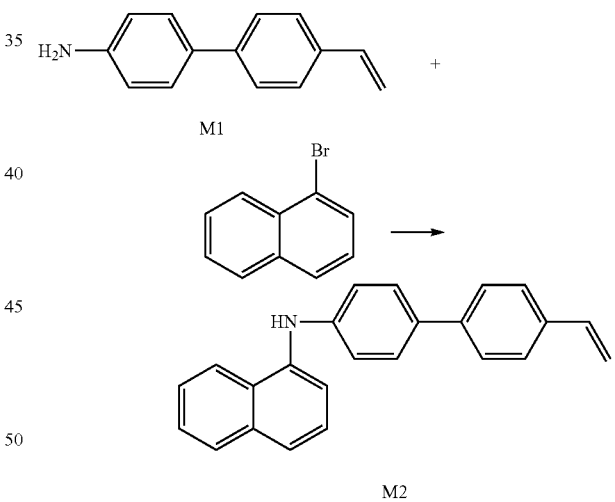

M2

In a 100 ml round-bottom flask, 0.5 g (2.56 mmol) of Compound M1, 0.63 g (3.0 mmol) of 2-bromonaphthalene, 1.14 g (5.6 mmol) of sodium tert-butoxide, 0.09 g (0.1 mmol) of tris(dibenzylideneacetone)dipalladium (0), and 14.8 mg (0.15 mmol) of tri-tert-butylphosphine were dissolved in 30 ml of toluene, and then the resulting solution was stirred in a bath at 60° C. for 5 hours. When the reaction was completed, toluene was removed, followed by column separation using dichloromethane and n-hexane, thereby obtaining 0.5 g (1.5 mmol) of Compound M2.

(3) Synthesis of Compound 1

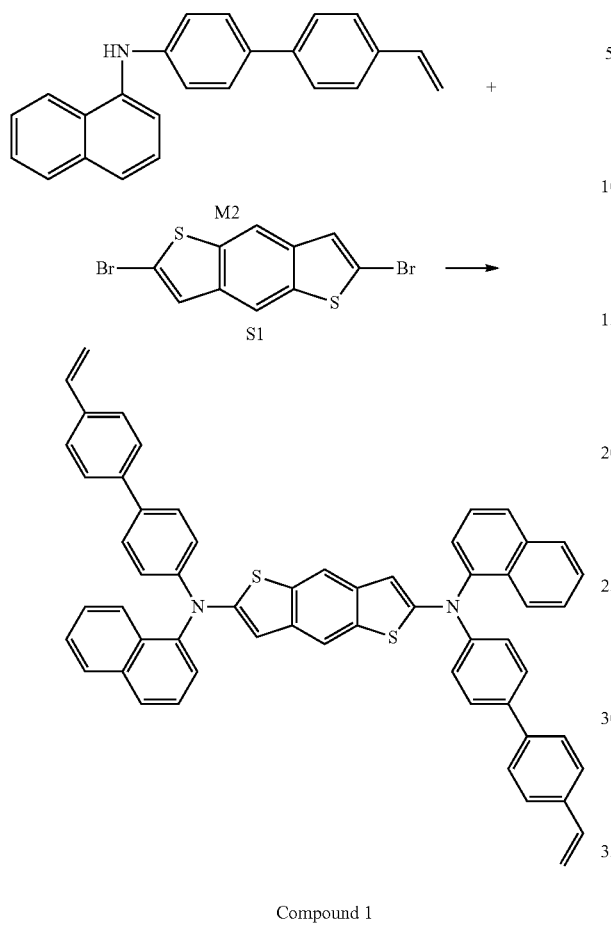

Compound 1

In a 50 ml round-bottom flask, 0.2 g (0.62 mmol) of Compound M2, 86.6 mg (0.25 mmol) of Compound S1, 0.13 g (0.62 mmol) of sodium tert-butoxide, 18.3 (0.02 mmol) of tris(dibenzylideneacetone)dipalladium (0), and 5.8 mg (0.06 mmol) of tri-tert-butylphosphine were dissolved in 20 ml of toluene, and then the resulting solution was stirred in a bath at 120° C. for 4 hours. When the reaction was completed, the reaction product was cooled to room temperature, filtered with a Celite/silica gel, concentrated, and separated by a column using dichloromethane and n-hexane, thereby obtaining 0.1 g (0.13 mmol) of Compound 1.

Synthesis Example 2: Synthesis of Compound 2

(1) Synthesis of Compound M3

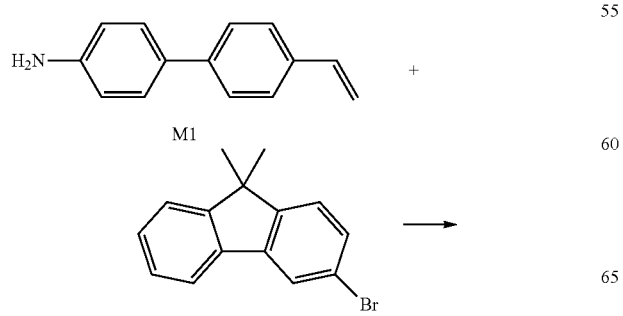

-continued

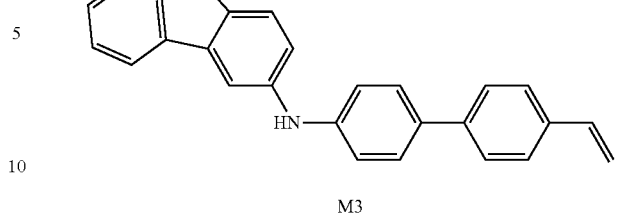

M3

In a 100 ml round-bottom flask, 0.5 g (2.56 mmol) of Compound M1, 0.82 g (3.0 mmol) of 3-bromo-9,9-dimethyl-9H-fluorene, 1.14 g (5.6 mmol) of sodium tert-butoxide, 0.09 g (0.1 mmol) of tris(dibenzylideneacetone)dipalladium (0), and 14.8 mg (0.15 mmol) of tri-tert-butylphosphine were dissolved in 30 ml of toluene, and then the resulting solution was stirred in a bath at 60° C. for 5 hours. When the reaction was completed, toluene was removed, followed by column separation using dichloromethane and n-hexane, thereby obtaining 0.47 g (1.2 mmol) of Compound M3.

(2) Synthesis of Compound 2

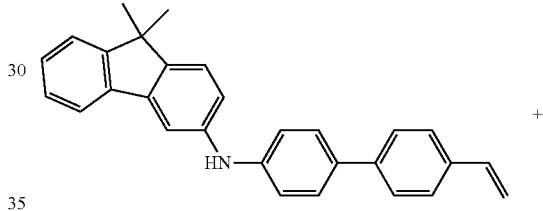

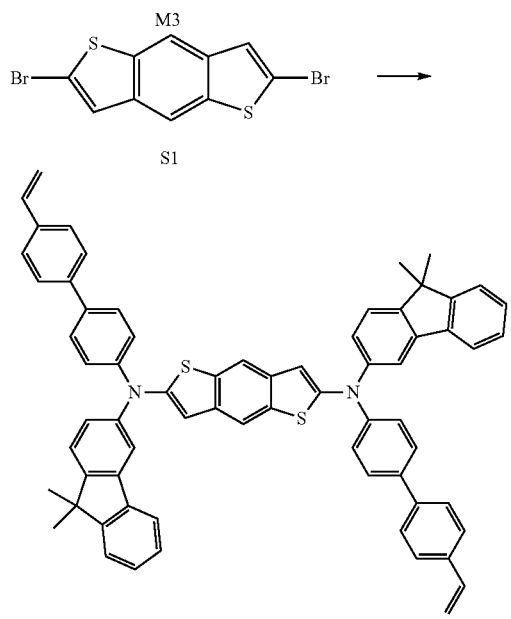

Compound 2

In a 50 ml round-bottom flask, 0.24 g (0.62 mmol) of Compound M3, 86.6 mg (0.25 mmol) of Compound S1, 0.13 g (0.62 mmol) of sodium tert-butoxide, 18.3 (0.02 mmol) of tris(dibenzylideneacetone)dipalladium (0), and 5.8 mg (0.06 mmol) of tri-tert-butylphosphine were dissolved in 20 ml of Synthesis Example 3: Synthesis of Compound 3

(1) Synthesis of Compound M4

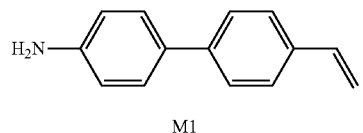

M1

In a 100 ml round-bottom flask, 0.5 g (2.56 mmol) of Compound M1, 0.97 g (3.0 mmol) of 9-(4-bromophenyl)-9H-carbazole, 1.14 g (5.6 mmol) of sodium tert-butoxide, 0.09 g (0.1 mmol) of tris(dibenzylideneacetone)dipalladium (0), and 14.8 mg (0.15 mmol) of tri-tert-butylphosphine were dissolved in 30 ml of toluene, and then the resulting solution was stirred in a bath at 60° C. for 5 hours. When the reaction was completed, toluene was removed, followed by column separation using dichloromethane and n-hexane, thereby obtaining 0.67 g (1.5 mmol) of Compound M4.

(2) Synthesis of Compound 3

In a 50 ml round-bottom flask, 0.27 g (0.62 mmol) of Compound M4, 86.6 mg (0.25 mmol) of Compound S1, 0.13 g (0.62 mmol) of sodium tert-butoxide, 18.3 (0.02 mmol) of tris(dibenzylideneacetone)dipalladium (0), and 5.8 mg (0.06 mmol) of tri-tert-butylphosphine were dissolved in 20 ml of toluene, and then the resulting solution was stirred in a bath at 120° C. for 4 hours. When the reaction was completed, the reaction product was cooled to room temperature, filtered with a Celite/silica gel, concentrated, and separated by a column using dichloromethane and n-hexane, thereby obtaining 0.1 g (0.11 mmol) of Compound 3.

Example 1

Manufacture of Light-Emitting Diode

A light-emitting diode was manufactured using Compound 1 synthesized according to Synthesis Example 1. As an anode, ITO glass (thickness: 50 nm) was patterned such that the ITO glass had a light-emitting area of 3 mm×3 mm, and then washed by treating with UV-ozone for 30 minutes. Subsequently, an emissive layer and a cathode were stacked according to the following order: a hole injection layer (HIL) (PEDOT:PSS, spin coating (2,000 rpm) and then drying at 120° C. for 30 minutes; 25 nm), a first hole transport layer (HTL1) (TFB (in toluene), spin coating (2,000 rpm) and then drying at 120° C. for 30 minutes; 25 nm), a second hole transport layer (HTL2) (Compound 1 of Synthesis Example 1 (in 1,2-dichloroethane), spin coating (2,000 rpm) and then drying at 120° C. for 30 minutes, followed by curing at 200° C. for 1 hour; 10 nm), an emitting material layer (EML) (ZnSe/ZnS (in hexane), spin coating (2,000 rpm) and then drying at 70° C. for 60 minutes; 20 nm), an electron transport layer (ZnO (in 2-methoxyethanol), spin coating (2,000 rpm) and then drying at 70° C. for 60 minutes; 50 nm), and a cathode (Al, deposition after a substrate with an emissive layer formed thereon was transferred to a vacuum chamber (3×10−6 Torr, 4-5 Å/s); 80 nm).

After deposition, for film formation, the resulting structure was moved from the deposition chamber into a dry box, followed by encapsulation using UV-curable epoxy and a moisture getter. The manufactured light-emitting diode has an emission area of 9 $mm^2$.

Example 2

Manufacture of Light-Emitting Diode

A light-emitting diode was manufactured in the same manner as in Example 1, except that Compound 2 synthesized according to Synthesis Example 2 was used instead of Compound 1.

Example 3

Manufacture of Light-Emitting Diode

A light-emitting diode was manufactured in the same manner as in Example 1, except that Compound 3 synthesized according to Synthesis Example 3 was used instead of Compound 1.

Comparative Example

Manufacture of Light-Emitting Diode

A light-emitting diode was manufactured in the same manner as in Example 1, except that the HTL2 was not applied.

Experimental Example

Evaluation of Physical Characteristics of Light-Emitting Diodes

Figure 7:
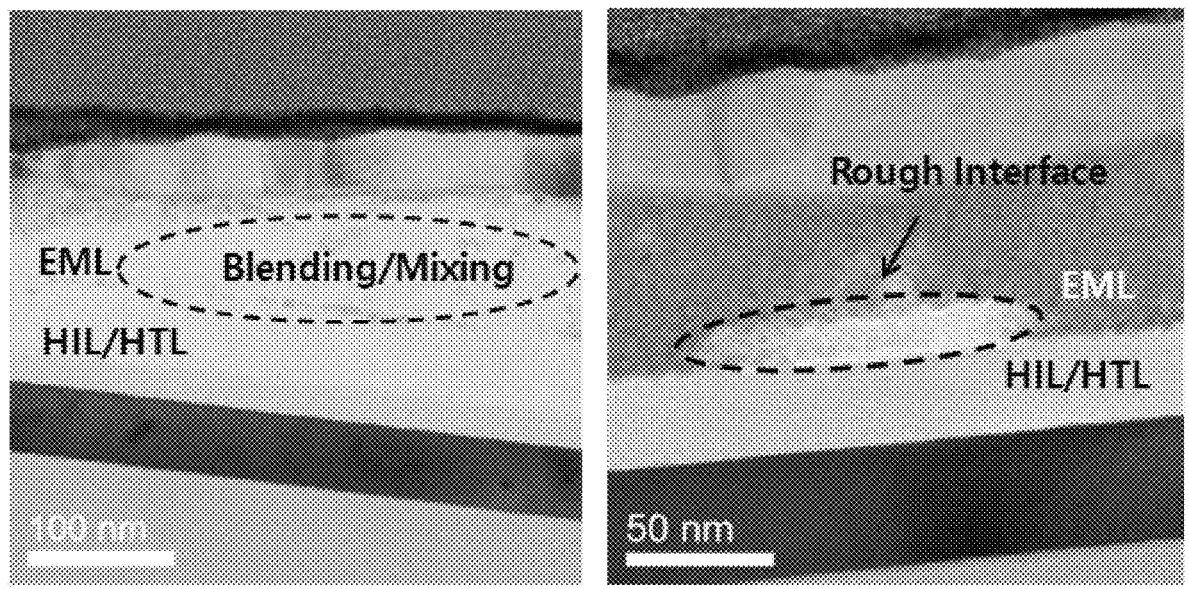
FIG. 7 is a transmission electron microscope (TEM) image showing a cross-sectional shape of an HTL, an EML, and an interface between these emissive layers in an existing light-emitting diode manufactured through a solution process.
Figure 8:
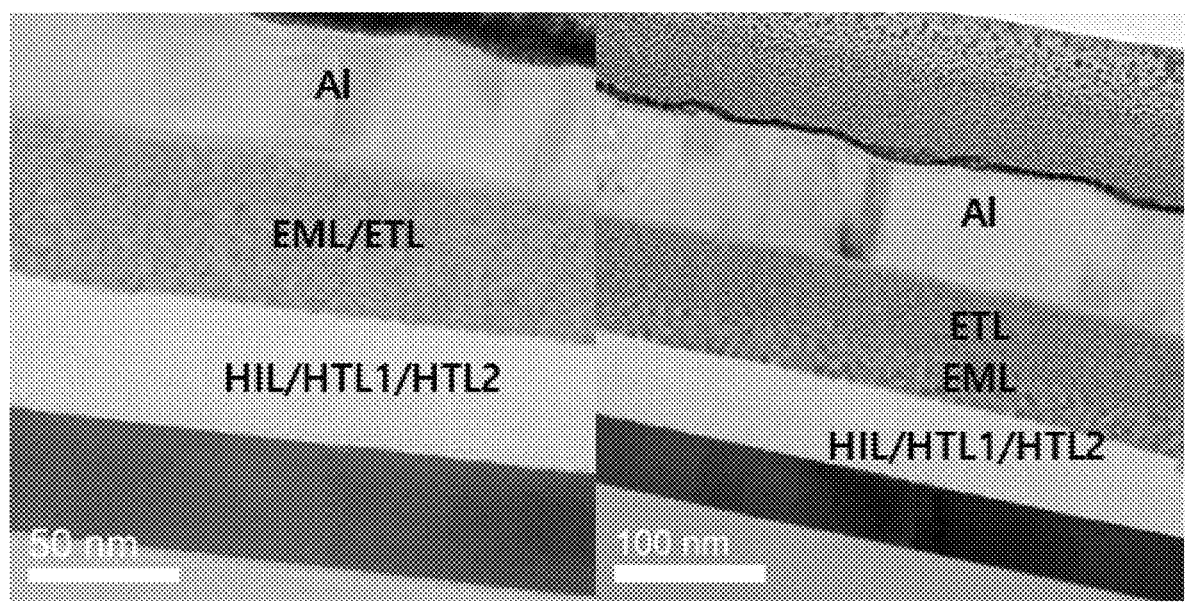
FIG. 8 is a TEM image showing a cross-sectional shape of an HTL, an EML, and an interface between these emissive layers in a light-emitting diode according to the present disclosure manufactured through a solution process.

First, a form of an interface between emissive layers constituting each of the light-emitting diodes manufactured according to Examples 1 to 3 and Comparative Example was measured using a transmission electron microscope (TEM). As illustrated in FIG. 7, in a case in which the organic compound synthesized according to the present disclosure is not used, materials constituting the HTL and the EML are mixed with each other, and thus the HTL and the EML are not distinctly distinguished from each other and an interface therebetween is unclearly formed and has a rough cross-sectional shape. In contrast, as illustrated in FIG. 8, when the cured product of the organic compound synthesized according to the present disclosure is applied to the HTL2 adjacent to the EML, mixing of materials constituting the HTL and the EML is prevented, and thus the HTL is distinctly distinguished from the EML. From these results, it is confirmed that the interface between the HTL and the EML is smoothly formed as intended and has a reduced roughness.

Figure 9:
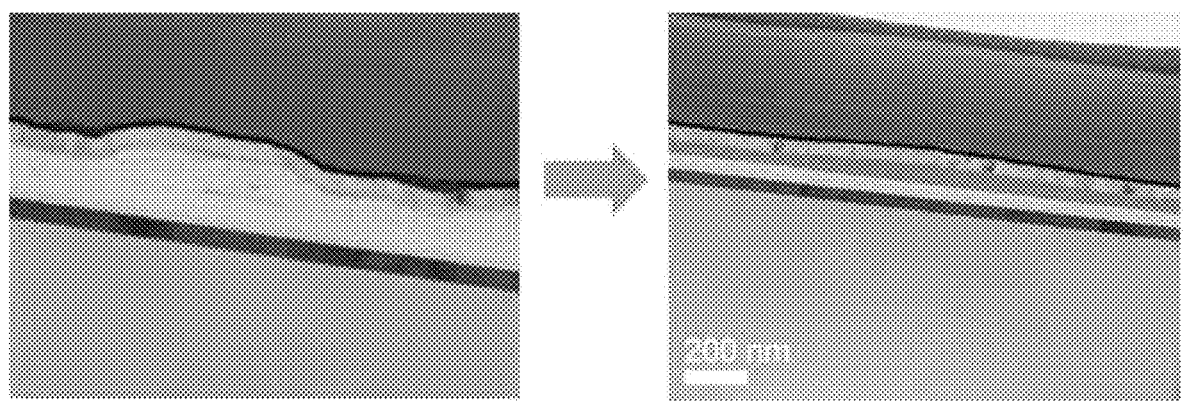
FIG. 9 is a cross-sectional view showing overall morphologies of an existing light-emitting diode manufactured through a solution process and a light-emitting diode in which a cured product of an organic compound according to the present disclosure is applied to an HTL, wherein the left image shows the existing light-emitting diode, and the right image shows the light-emitting diode manufactured according to the present disclosure.

As illustrated in the left image of FIG. 9, when observing an overall cross-sectional shape of the light-emitting diode of Comparative Example, a partial region of an interface between emissive layers has a rough and curved cross-sectional shape, which indicates poor morphological characteristics. In contrast, as illustrated in the right image of FIG. 9, it was confirmed that an interface between emissive layers constituting each of the light-emitting diodes of Examples 1 to 3 maintained a smooth cross-sectional shape and each light-emitting diode exhibited significantly enhanced morphological characteristics.

In addition, each of the light-emitting diodes of Examples 1 to 3 and Comparative Example was connected to an external power source, and electroluminescent (EL) characteristics of all the diodes manufactured in the present disclosure were evaluated using a constant current source (KEITHLEY) and a photometer PR650 at room temperature. In particular, driving voltage (V), current (A), current density ($mA/m^2$), external quantum efficiency (EQE), and luminance ($cd/m^2$) of the light-emitting diodes of Examples 1 to 3 and Comparative Example were measured. The results thereof are shown in Table 1 below.

TABLE 1

EL Characteristics of Light-Emitting Diodes

| Sample | HTL1/HTL2 | V | A | Max $mA/m^2$ | EQE | $cd/m^2$ |
|---|---|---|---|---|---|---|
| Example 1 | TFB/Compound 1 | 6 | 0.0789 | 876.8 | 0.0108 | 112.90 |
| Example 2 | TFB/Compound 2 | 6 | 0.0815 | 906.0 | 0.0336 | 213.60 |
| Example 3 | TFB/Compound 3 | 5 | 0.0715 | 793.9 | 0.0209 | 167.20 |
| Comparative Example | TFB/— | 13 | 0.0150 | 166.8 | 0.0038 | 8.13 |

As shown in Table 1, when the cured product of the organic compound synthesized according to the present disclosure was applied to the HTL2, a voltage exhibiting a maximum efficiency was reduced by 61.5%, compared to the light-emitting diode to which only the HTL1 formed of TFB was applied. In addition, a maximum 4.4-fold increase in current, a maximum 4.4-fold increase in current density, a maximum 7.84-fold increase in EQE, and a maximum 25.3-fold increase in luminance were exhibited. From these results, it was confirmed that a light-emitting diode and a light-emitting device suitable for low-voltage operation and having significantly enhanced luminous efficiency and quantum efficiency could be realized by applying a cross-linked cured product of the organic compounds synthesized according to the present disclosure to an HTL.

As is apparent from the foregoing description, the present disclosure provides an organic compound having excellent hole transfer properties and high thermal stability and capable of forming crosslinks by a curing process, and a light-emitting diode and a light-emitting device in which a cured product of the organic compound is applied to a hole transfer layer.

The organic compound according to the present disclosure can be converted into a cured product that forms rigid crosslinks by a curing process. Thus, when the cured product of the organic compound according to the present disclosure is applied to a hole transfer layer adjacent to an emitting material layer, an intermediate layer formed of the cured product of the organic compound synthesized according to the present disclosure can be formed between the emitting material layer and the hole transfer layer, to which a solution process can be applied, and accordingly, mixing of materials constituting the emitting material layer and the hole transfer layer can be prevented.

Since materials constituting neighboring emissive layers formed by a solution process are not mixed, an interface between the respective emissive layers is not roughly, but smoothly formed, and thus the interface between the emissive layers can exhibit significantly reduced roughness. The respective emissive layers are clearly distinguished from each other, overall morphological characteristics of the light-emitting diode can be enhanced, and charges can be injected in balance into the entire region of the light-emitting diode.

Excitons may be effectively formed in the emitting material layer without loss of holes and electrons, thereby contributing to luminescence. Accordingly, a light-emitting diode and a light-emitting device that have enhanced luminous efficiency, and can be operated at low voltage, and reduce power consumption can be realized and manufactured.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the disclosure. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A light-emitting diode, comprising:
a first electrode;
a hole injection layer;
a hole transport layer;
an emitting material layer;
an electron transport layer; and
a second electrode,
wherein the hole transport layer comprises a cross-linked compound derived from a compound having the following structure of Formula 1:

Formula 1

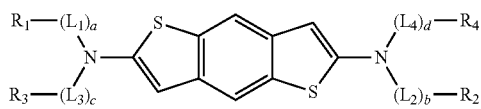

wherein:
$R_1$ and $R_2$ are each independently

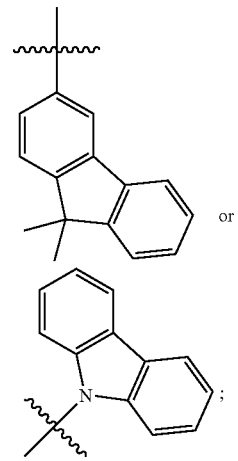

$R_3$ and $R_4$ are each independently

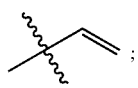 [SMILES: *C=C]

$L_1$, $L_2$, $L_3$, and $L_4$ are each independently

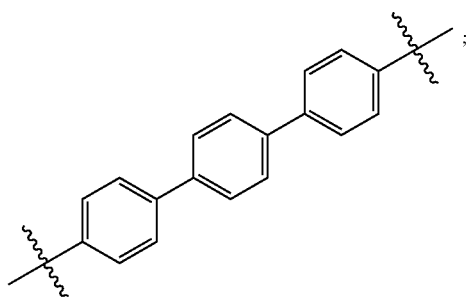

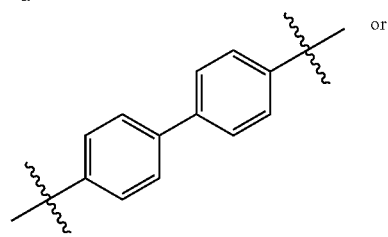

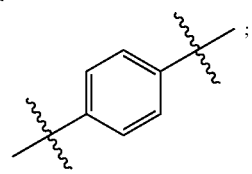

a and b are each independently 0 or 1;
c and d are each independently 1 or 2, and
wherein:
the hole injection layer consists of poly(ethylenedioxythiophene):polystyrenesulfonate;

the hole transport layer comprises:
  a first hole transport layer over the hole injection layer, and
  a second hole transport layer over the first hole transport layer; and
the second hole transport layer consists of the cross-linked compound.

2. The light-emitting diode of claim 1, wherein a and b are both 0.

3. The light-emitting diode of claim 1, wherein a is 1 and $L_1$ has the following structure:

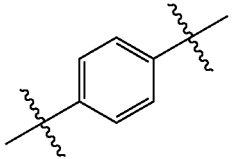

4. The light-emitting diode of claim 1, wherein b is 1 and $L_2$ has the following structure:

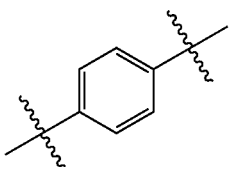

5. The light-emitting diode of claim 1, wherein c is 1 and $L_3$ has one of the following structures:

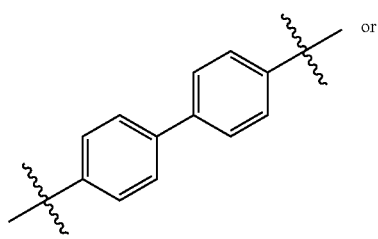

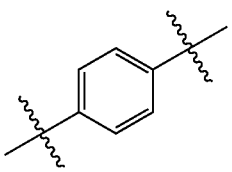

6. The light-emitting diode of claim 1, wherein d is 1 and $L_4$ has one of the following structures:

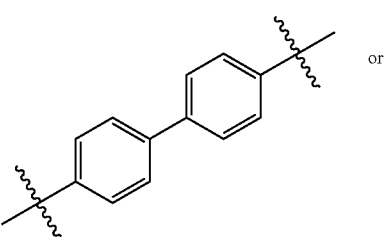

-continued

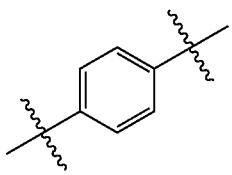

7. The light-emitting diode of claim 1, wherein the compound has one of the following structures:

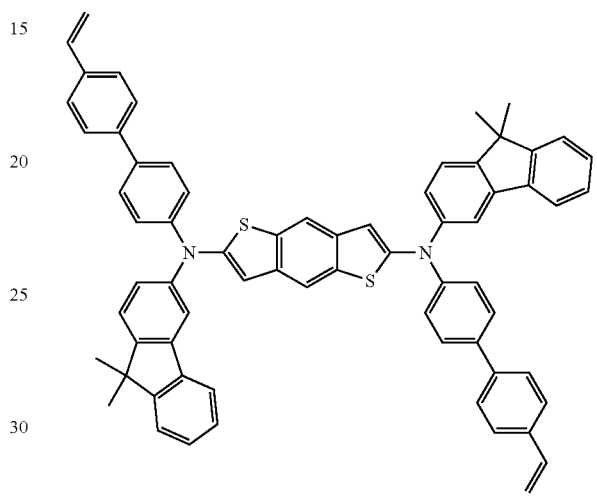

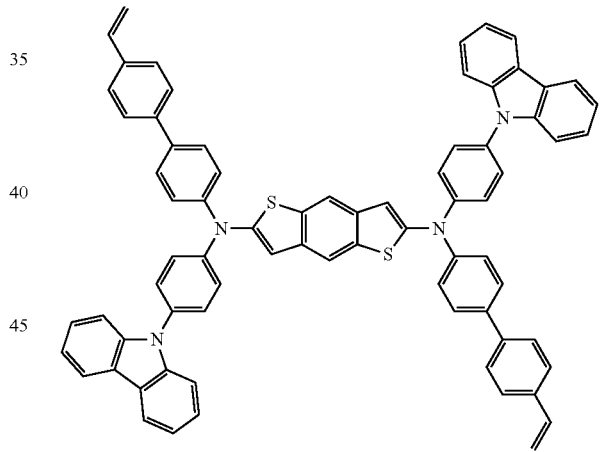

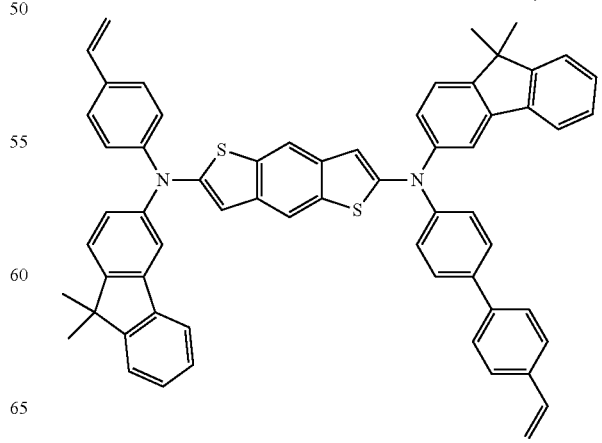

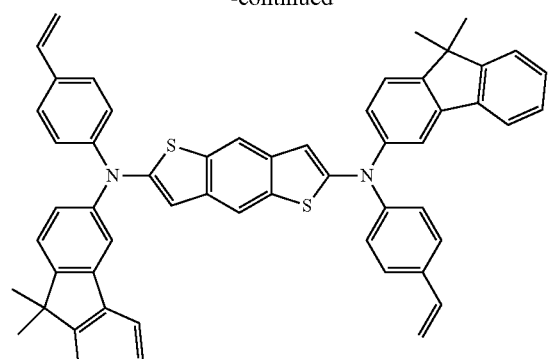
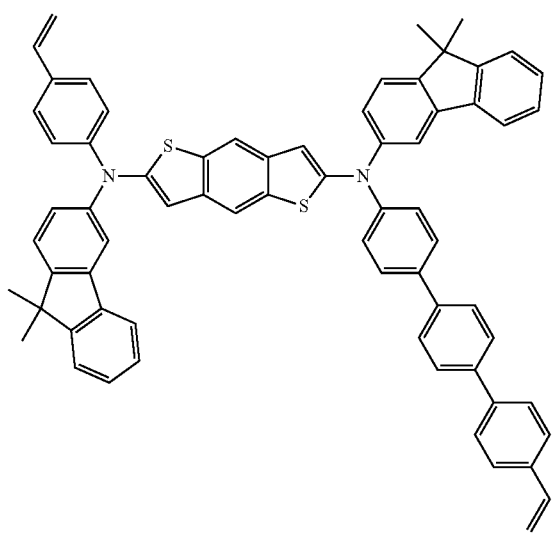 [SMILES: C=Cc1ccc(-c2ccc(-c3ccc(N(c4ccc5c(c4)-c4ccccc4C5(C)C)c4cc5cc6sc(N(c7ccc(C=C)cc7)c7ccc8c(c7)-c7ccccc7C8(C)C)cc6cc5s4)cc3)cc2)cc1]
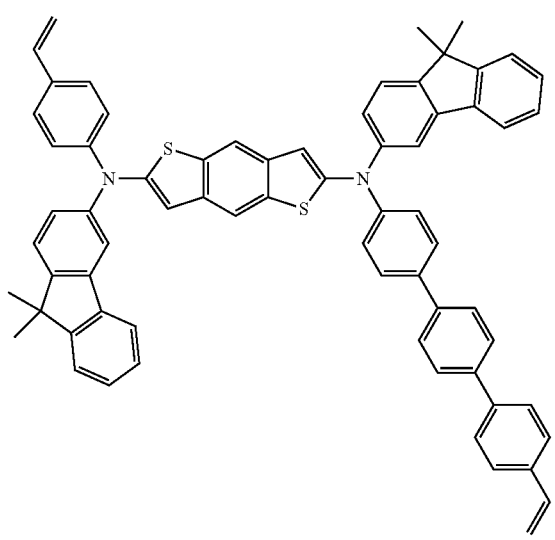
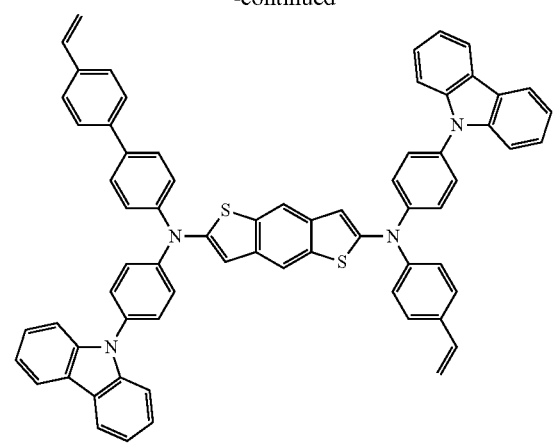
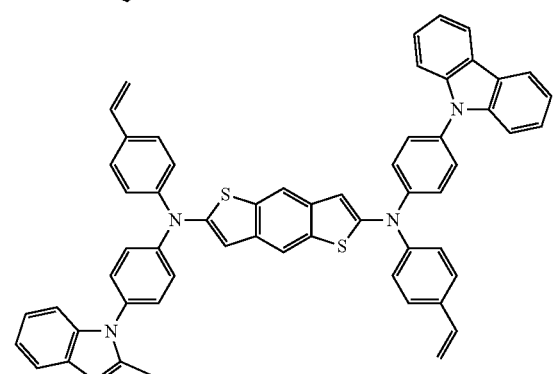
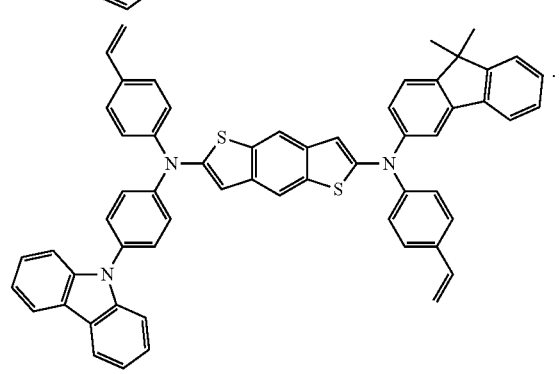
8. The light-emitting diode of claim 1, wherein each of c and d is 1,
L₃ is
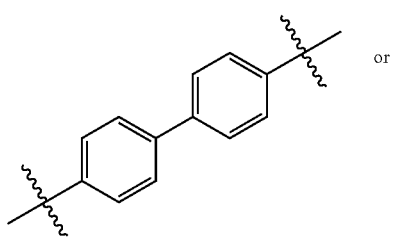
or -continued

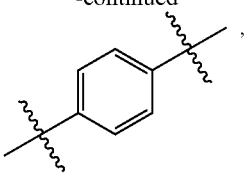

and

L₄ is

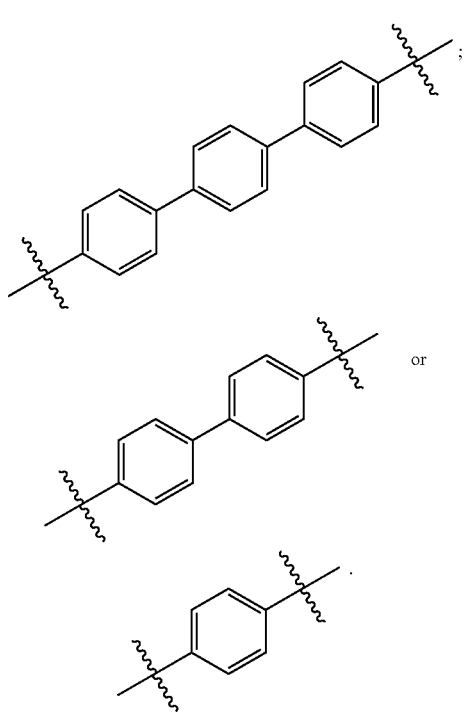

9. The light-emitting diode of claim 1, wherein the first hole transport layer comprises a hole transporting material having one of the following structures:

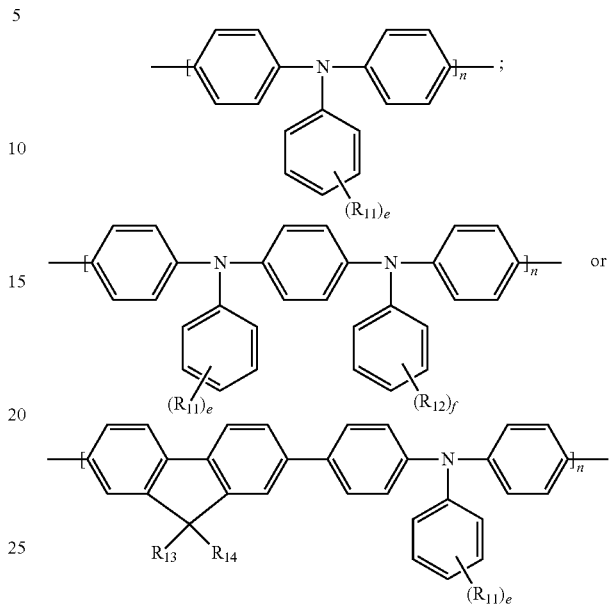

wherein:

$R_{11}$, $R_{12}$, $R_{13}$, and $R_{14}$ are each independently an unsubstituted or substituted linear or branched $C_1$-$C_{20}$ alkyl group, an unsubstituted or substituted $C_1$-$C_{20}$ alkoxy group, an unsubstituted or substituted $C_5$-$C_{30}$ aryl group, or an unsubstituted or substituted $C_4$-$C_{30}$ heteroaryl group;

e and f are each independently an integer of 1 to 4; and n is an integer of 1 or more.

10. The light-emitting diode of claim 1, wherein the hole transport layer comprises a host material and a dopant, the cross-linked compound present as the dopant.

* * * * *